United States Patent
Maurer, Jr. et al.

(10) Patent No.: US 10,500,415 B2
(45) Date of Patent: Dec. 10, 2019

(54) GANTRY IMAGE GUIDED RADIOTHERAPY SYSTEM AND RELATED TREATMENT DELIVERY METHODS

(71) Applicant: ACCURAY INCORPORATED, Sunnyvale, CA (US)

(72) Inventors: Calvin R. Maurer, Jr., San Jose, CA (US); Euan S. Thomson, Los Gatos, CA (US)

(73) Assignee: ACCURAY INCORPORATED, Sunnyvale, CA (US)

( * ) Notice: Subject to any disclaimer, the term of this patent is extended or adjusted under 35 U.S.C. 154(b) by 0 days.

(21) Appl. No.: 15/875,683

(22) Filed: Jan. 19, 2018

(65) Prior Publication Data
US 2018/0178037 A1    Jun. 28, 2018

Related U.S. Application Data

(60) Continuation of application No. 15/078,553, filed on Mar. 23, 2016, which is a division of application No.
(Continued)

(51) Int. Cl.
*A61N 5/10* (2006.01)
*A61B 6/00* (2006.01)
(Continued)

(52) U.S. Cl.
CPC .......... *A61N 5/1039* (2013.01); *A61B 5/0035* (2013.01); *A61B 5/0059* (2013.01);
(Continued)

(58) Field of Classification Search
CPC .......... A61B 6/04; A61B 6/0407; A61B 6/44; A61N 5/1048; A61N 5/1049;
(Continued)

(56) References Cited

U.S. PATENT DOCUMENTS 2,890,349 A   6/1959   Huszar
2,950,394 A   8/1960   Stava
(Continued)

FOREIGN PATENT DOCUMENTS

DE   102008030893   12/2009
EP   1 419 801   5/2004
(Continued)

OTHER PUBLICATIONS

USPTO, Non-Final Office Action for U.S. Appl. No. 13/033,571(L429) dated Jun. 26, 2013, 26 pages.
(Continued)

*Primary Examiner* — Thomas R Artman
(74) *Attorney, Agent, or Firm* — Womble Bond Dickinson (US) LLP; Daniel E. Ovanezian

(57) ABSTRACT

A radiation treatment apparatus, comprising a gantry structure comprising a beam member extending between first and second ends of the gantry structure. The radiation treatment apparatus also includes a radiation treatment head movably mounted to the beam member in a manner that allows (i) translation of the radiation treatment head along the beam member between the first and second ends, and (ii) gimballing of the radiation treatment head relative to the beam member, the gimballing comprising pivotable movement in at least one independent pivot direction defined with respect to the beam member. The radiation treatment apparatus also includes a patient couch operative coupled with the radiation treatment head in manner to provide movement of the patient couch relative to the radiation treatment head.

17 Claims, 22 Drawing Sheets

Related U.S. Application Data

14/548,095, filed on Nov. 19, 2014, now Pat. No. 9,327,141, which is a division of application No. 13/033,584, filed on Feb. 23, 2011, now Pat. No. 8,934,605.

(60) Provisional application No. 61/371,732, filed on Aug. 8, 2010, provisional application No. 61/307,847, filed on Feb. 24, 2010.

(51) Int. Cl.
| | |
|---|---|
| *A61B 6/06* | (2006.01) |
| *A61B 5/00* | (2006.01) |
| *A61B 5/055* | (2006.01) |
| *A61B 6/02* | (2006.01) |
| *A61B 6/03* | (2006.01) |

(52) U.S. Cl.
CPC .............. *A61B 5/055* (2013.01); *A61B 6/025* (2013.01); *A61B 6/032* (2013.01); *A61B 6/06* (2013.01); *A61B 6/4014* (2013.01); *A61B 6/4085* (2013.01); *A61B 6/4435* (2013.01); *A61B 6/4452* (2013.01); *A61B 6/488* (2013.01); *A61N 5/10* (2013.01); *A61N 5/1042* (2013.01); *A61N 5/1048* (2013.01); *A61N 5/1049* (2013.01); *A61N 5/1065* (2013.01); *A61N 5/1067* (2013.01); *A61N 5/1081* (2013.01); *A61N 5/1082* (2013.01); *A61N 5/1037* (2013.01); *A61N 2005/1061* (2013.01); *A61N 2005/1062* (2013.01); *A61N 2005/1092* (2013.01); *G01N 2223/308* (2013.01)

(58) Field of Classification Search
CPC .... A61N 5/1064; A61N 5/1067; A61N 5/107; A61N 2005/1061; A61N 2005/1062
See application file for complete search history.

(56) References Cited

U.S. PATENT DOCUMENTS

| | | | |
|---|---|---|---|
| 3,082,322 A * | 3/1963 | Koerner | A61N 5/01 378/196 |
| 3,466,439 A | 9/1969 | Edvard | |
| 4,651,007 A | 3/1987 | Perusek et al. | |
| 5,027,818 A | 7/1991 | Bova et al. | |
| 5,099,134 A | 3/1992 | Hase | |
| 5,189,687 A | 2/1993 | Bova et al. | |
| 5,207,223 A * | 5/1993 | Adler | A61B 6/08 600/427 |
| 5,380,336 A | 1/1995 | Misko et al. | |
| 5,427,097 A * | 6/1995 | Depp | A61N 5/1049 600/427 |
| 5,464,013 A | 11/1995 | Lemelson | |
| 5,634,929 A | 6/1997 | Misko et al. | |
| 5,724,400 A | 3/1998 | Swerdloff et al. | |
| 5,727,042 A * | 3/1998 | Brenneisen | A61N 5/1049 378/208 |
| 5,818,902 A | 10/1998 | Yu | |
| 6,075,840 A | 6/2000 | Pellegrino | |
| 6,269,143 B1 | 7/2001 | Tachibana | |
| RE37,474 E | 12/2001 | Hug et al. | |
| 6,385,288 B1 | 5/2002 | Kanematsu | |
| 6,501,981 B1 | 12/2002 | Schweikard et al. | |
| 6,614,871 B1 | 9/2003 | Kobiki et al. | |
| 6,647,092 B2 | 11/2003 | Eberhard | |
| 6,778,850 B1 | 8/2004 | Adler | |
| 6,865,254 B2 | 3/2005 | Nafstadius | |
| 6,885,724 B2 | 4/2005 | Li | |
| 6,969,194 B1 | 11/2005 | Nafstadius | |
| 6,973,158 B2 | 12/2005 | Besson | |
| 6,973,202 B2 | 12/2005 | Mostafavi | |
| 6,977,987 B2 | 12/2005 | Yamashita | |
| 7,085,347 B2 * | 8/2006 | Mihara | A61N 5/10 378/197 |
| 7,142,633 B2 | 11/2006 | Eberhard | |
| 7,162,008 B2 | 1/2007 | Earl | |
| 7,188,999 B2 | 1/2007 | Mihara et al. | |
| 7,193,227 B2 | 3/2007 | Hiramoto et al. | |
| 7,204,640 B2 | 4/2007 | Fu et al. | |
| 7,212,608 B2 | 5/2007 | Nagamine et al. | |
| 7,212,609 B2 | 5/2007 | Nagamine et al. | |
| 7,218,702 B2 | 5/2007 | Mistretta et al. | |
| 7,227,925 B1 | 6/2007 | Mansfield et al. | |
| 7,231,017 B2 | 6/2007 | Gertsenshteyn | |
| 7,239,684 B2 | 7/2007 | Hara et al. | |
| 7,245,698 B2 | 7/2007 | Pang et al. | |
| 7,246,943 B2 | 7/2007 | Gotoh | |
| 7,265,356 B2 | 9/2007 | Pelizzari et al. | |
| 7,302,033 B2 | 11/2007 | Carrano | |
| 7,345,282 B2 | 3/2008 | Hawman | |
| 7,349,730 B2 | 3/2008 | Ein-Gal | |
| 7,388,940 B1 | 6/2008 | De Man | |
| 7,405,407 B2 | 7/2008 | Hiramoto et al. | |
| 7,436,928 B2 | 10/2008 | Urano et al. | |
| 7,440,603 B2 | 10/2008 | Eberhard | |
| 7,444,011 B2 | 10/2008 | Pan et al. | |
| 7,446,328 B2 | 11/2008 | Rigney | |
| 7,471,765 B2 | 12/2008 | Jaffray et al. | |
| 7,505,562 B2 | 3/2009 | Dinca et al. | |
| 7,519,149 B2 | 4/2009 | Mackie et al. | |
| 7,519,151 B1 | 4/2009 | Shukla | |
| 7,532,705 B2 | 5/2009 | Yin et al. | |
| 7,545,911 B2 | 6/2009 | Rietzel et al. | |
| 7,564,945 B2 | 7/2009 | Kim | |
| 7,567,647 B1 | 7/2009 | Maltz | |
| 7,577,233 B1 | 8/2009 | Tsang et al. | |
| 7,623,623 B2 * | 11/2009 | Raanes | A61N 5/1049 378/205 |
| 7,639,777 B2 | 12/2009 | Warner | |
| 7,639,853 B2 | 12/2009 | Olivera et al. | |
| 7,640,607 B2 | 1/2010 | Guertin et al. | |
| 7,657,304 B2 | 2/2010 | Mansfield | |
| 7,668,292 B1 | 2/2010 | Bose et al. | |
| 7,672,429 B2 | 3/2010 | Urano et al. | |
| 7,679,073 B2 | 3/2010 | Urano et al. | |
| 7,684,647 B2 | 3/2010 | Fu et al. | |
| 7,693,257 B2 | 4/2010 | Allison | |
| 7,711,087 B2 | 5/2010 | Mostafavi | |
| 7,801,269 B2 | 9/2010 | Cravens et al. | |
| 7,831,013 B2 | 11/2010 | Star-Lack et al. | |
| 7,876,881 B2 | 1/2011 | Jeffrey | |
| 7,902,530 B1 | 3/2011 | Sahadevan | |
| 7,961,838 B2 | 6/2011 | Yin | |
| 7,978,817 B2 | 7/2011 | Rietzel | |
| 7,983,380 B2 | 7/2011 | Guertin et al. | |
| 8,079,100 B2 * | 12/2011 | Herrmann | A61N 5/1049 378/206 |
| 8,130,907 B2 | 3/2012 | Maurer et al. | |
| 8,244,330 B2 | 8/2012 | Meier et al. | |
| 8,254,521 B2 | 8/2012 | Brooks et al. | |
| 8,340,742 B2 | 12/2012 | Meier et al. | |
| 8,515,004 B2 | 8/2013 | Star-Lack et al. | |
| 8,559,596 B2 | 10/2013 | Thomson et al. | |
| 9,616,248 B2 | 4/2017 | Meier et al. | |
| 9,682,253 B2 | 6/2017 | Meier et al. | |
| 9,700,740 B2 * | 7/2017 | Maurer, Jr. | A61N 5/10 |
| 10,173,078 B2 | 1/2019 | Mauer et al. | |
| 2002/0154728 A1 | 10/2002 | Morita et al. | |
| 2003/0048868 A1 | 3/2003 | Bailey et al. | |
| 2004/0005027 A1 | 1/2004 | Nafstadius | |
| 2004/0037390 A1 | 2/2004 | Mihara et al. | |
| 2004/0170254 A1 | 9/2004 | Gregerson et al. | |
| 2004/0184579 A1 | 9/2004 | Mihara et al. | |
| 2004/0184583 A1 | 9/2004 | Nagamine et al. | |
| 2005/0049478 A1 | 3/2005 | Kuduvalli et al. | |
| 2005/0078861 A1 | 4/2005 | Usikov | |
| 2005/0117708 A1 | 6/2005 | Cho | |
| 2005/0226364 A1 | 10/2005 | De Man | |
| 2006/0002509 A1 | 1/2006 | Claus et al. | |
| 2006/0008047 A1 | 1/2006 | Zhou | |

(56) References Cited

U.S. PATENT DOCUMENTS

| | | |
|---|---|---|
| 2006/0058648 A1 | 3/2006 | Meier et al. |
| 2006/0074301 A1 | 4/2006 | Meier et al. |
| 2006/0074302 A1 | 4/2006 | Meier et al. |
| 2006/0098855 A1 | 5/2006 | Gkanatsios et al. |
| 2006/0163495 A1 | 7/2006 | Hiramoto et al. |
| 2006/0173294 A1 | 8/2006 | Ein-Gal |
| 2006/0203958 A1 | 9/2006 | Nagamine et al. |
| 2006/0210015 A1 | 9/2006 | Pelc |
| 2007/0003010 A1 | 1/2007 | Guertin et al. |
| 2007/0003123 A1 | 1/2007 | Fu |
| 2007/0014391 A1 | 1/2007 | Mostafavi et al. |
| 2007/0016014 A1 | 1/2007 | Hara et al. |
| 2007/0025509 A1 | 2/2007 | Pang et al. |
| 2007/0041500 A1 | 2/2007 | Olivera et al. |
| 2007/0076846 A1 | 4/2007 | Ruchala |
| 2007/0116175 A1 | 5/2007 | Zhang et al. |
| 2007/0189591 A1 | 8/2007 | Lu |
| 2007/0195930 A1 | 8/2007 | Kapatoes et al. |
| 2007/0211856 A1 | 9/2007 | Urano et al. |
| 2007/0211857 A1 | 9/2007 | Urano et al. |
| 2007/0237290 A1 | 10/2007 | Mostafavi |
| 2007/0242801 A1 | 10/2007 | Mackie et al. |
| 2007/0253523 A1 | 11/2007 | Zamyatin |
| 2007/0291895 A1 | 12/2007 | Yin et al. |
| 2007/0297566 A1 | 12/2007 | Urano et al. |
| 2008/0056435 A1 | 3/2008 | Basu |
| 2008/0071420 A1 | 3/2008 | Guertin et al. |
| 2008/0083871 A1 | 4/2008 | Cravens et al. |
| 2008/0101669 A1 | 5/2008 | Jeung |
| 2008/0130825 A1 | 6/2008 | Fu et al. |
| 2008/0170663 A1 | 7/2008 | Urano et al. |
| 2008/0197303 A1 | 8/2008 | Aoi et al. |
| 2008/0197304 A1 | 8/2008 | Urano et al. |
| 2008/0240350 A1 | 10/2008 | Moyers |
| 2008/0260093 A1 | 10/2008 | Bontus |
| 2009/0003512 A1 | 1/2009 | Pouliot et al. |
| 2009/0003522 A1 | 1/2009 | Chien et al. |
| 2009/0003523 A1* | 1/2009 | Raanes ............... A61N 5/1049 378/65 |
| 2009/0074134 A1 | 3/2009 | Jeffrey |
| 2009/0080603 A1 | 3/2009 | Shukla et al. |
| 2009/0110145 A1 | 4/2009 | Lu et al. |
| 2009/0110238 A1 | 4/2009 | Li |
| 2009/0116616 A1 | 5/2009 | Lu |
| 2009/0122963 A1* | 5/2009 | Herrmann ........... A61N 5/1049 378/209 |
| 2009/0175562 A1 | 7/2009 | Pan et al. |
| 2009/0180666 A1 | 7/2009 | Sheng |
| 2009/0226060 A1 | 9/2009 | Gering et al. |
| 2009/0252291 A1 | 10/2009 | Lu et al. |
| 2009/0296886 A1 | 12/2009 | Maltz et al. |
| 2009/0297011 A1 | 12/2009 | Brunner |
| 2010/0020931 A1 | 1/2010 | Otto |
| 2010/0040197 A1 | 2/2010 | Maniawski et al. |
| 2010/0053208 A1 | 3/2010 | Menningen et al. |
| 2010/0054409 A1 | 3/2010 | Bose et al. |
| 2010/0067739 A1 | 3/2010 | Mostafavi |
| 2010/0069742 A1 | 3/2010 | Partain |
| 2010/0091938 A1 | 4/2010 | Fadler |
| 2010/0104068 A1 | 4/2010 | Kilby et al. |
| 2010/0128839 A1 | 5/2010 | Partain |
| 2010/0172468 A1 | 7/2010 | Gregerson |
| 2010/0176309 A1 | 7/2010 | Mackie et al. |
| 2010/0228116 A1 | 9/2010 | Lu et al. |
| 2010/0246767 A1 | 9/2010 | Tanabe |
| 2011/0058647 A1 | 3/2011 | Star-Lack et al. |
| 2011/0210261 A1 | 9/2011 | Maurer, Jr. |
| 2011/0301449 A1 | 12/2011 | Maurer, Jr. |
| 2011/0313231 A1 | 12/2011 | Guertin et al. |
| 2012/0189102 A1 | 7/2012 | Maurer et al. |
| 2012/0330087 A1 | 12/2012 | Gregerson |
| 2013/0172657 A1 | 7/2013 | Meier et al. |
| 2017/0273643 A1* | 9/2017 | Maurer, Jr. .......... A61N 5/1081 |

FOREIGN PATENT DOCUMENTS

| | | |
|---|---|---|
| EP | 1419799 | 5/2004 |
| EP | 1946795 | 7/2008 |
| EP | 2058027 | 5/2009 |
| EP | 1472702 | 12/2009 |
| WO | 0074779 | 12/2000 |
| WO | 2008/106484 | 9/2008 |
| WO | 2009012453 | 1/2009 |
| WO | 2010030397 | 3/2010 |
| WO | 2011/106433 | 9/2011 |

OTHER PUBLICATIONS

USPTO, Final Office Action for U.S. Appl. No. 13/033,571(L429) dated Feb. 3, 2014, 17 pages.

USPTO, Notice of Allowance for U.S. Appl. No. 13/033,571 (L429) dated May 9, 2014.

USPTO, Non-Final Office Action for U.S. Appl. No. 13/088,289 (L445) dated Jun. 6, 2013, 20 pages.

USPTO, Non-Final Office Action for U.S. Appl. No. 13/088,289 (L445) dated Sep. 17, 2013, 20 pages.

USPTO, Final Office Action for U.S. Appl. No. 13/088,289 (L445) dated Apr. 30, 2014, 30 pages.

International Preliminary Report on Patentability for PCT Application No. PCT/US2012/020795, dated Aug. 1, 2013 L445PCT).

International Search Report and Written Opinion for for PCT Application No. PCT/US2012/020795 dated Jul. 13, 2012 (L445PCT).

International Search Report for PCT/US2011/025936, dated Aug. 11, 2011, 17 pgs.

Badea, Cristian C., "Volume Imaging Using a Combined Cone Beam CT-DTS Approach," Doctorate Thesis, University of Patras (2000).

Chen, Y., et. al., "Impulse Response Analysis for Several Digital Tomosynthesis Mammography Reconstruction Algorithms," Medical Imaging 2005: Physics of Medical Imaging, Michael J. Flynn, ed., Proceedings of SPIE vol. 5745, pp. 541-549 (2005).

Godfrey, D. et. al., "Digital Tomosynthesis With an On-Board Kilovoltage Imaging Device," Int. J. Radiation Oncology Biol. Phys., vol. 65, No. 1, pp. 8-15 (2006).

Kamino, Y., et. al., "Development of a Four-Dimensional Image-Guided Radiotherapy System With a Gimbaled X-Ray Head," Int. J. Radiation Oncology Biol. Phys., vol. 66, No. 1, pp. 271-278 (2006).

Kamino, Y., et. al., "Development of a New Concept Automatic Frequency Controller for an Ultrasmall C-Band Linear Accelerator Guide," Med. Phys. 34 (8), pp. 3243-3248 (Aug. 2007).

Kamino, Y., et. al., "Development of an Ultrasmall C-Bind Linear Accelerator' Guide for a Four-Dimensional Image-Guided Radiotherapy System With a Gimbaled X-Ray Head," Med. Phys. 34 (5), pp. 1797-1808 (May 2007).

Kilby et al., "The CyberKnife.RTM. Robotic Radiosurgery System in 2010", Tech. in Cancer Res. and Treatment vol. 9, No. 5, pp. 433-452 (2010).

Lalush, D., "Three-Dimensional Tomosynthesis Reconstruction from 1D and 2D X-ray Source Arrays," 2006 IEEE Nuclear Science Symposium Conference Record, pp. 1670-1674 (2006).

Martin et al., "Stereotactic Body Radiotherapy: A Review", Clinical Oncology pp. 1-16 (2010).

Poulot, J., "MV Cone Beam CT Imaging for Daily Localization: (Part II)," /.\APM CE-Therapy Series Panel Session Jul. 28, 2009, downloaded from hftp://www.aapm.org/meetings/amos2/pdf/42-12003-41828-461.pdf on Mar. 23, 2010 (Jul. 28, 2009).

Quan, E., et. al., "Three-Dimensional Imaging Properties of Rotation-Free Square and Hexagonal Micro-CT Systems," IEEE Trans. Med. Imaging, vol. 29, No. 3, pp. 916-923 (Mar. 2010).

Stellaray, "Digitally Addressable Flat Panel X-ray Sources for Medical Imaging," Stellaray, Inc., 1-page document, www.stellarray.com (undated).

Triple Ring Technologies, "Technology and Product Development: Focus on X-Ray Technologies," 2-page document, www.tripleringtech.com (undated).

(56) References Cited

OTHER PUBLICATIONS

Wang, J., "Accurate and Fast Localization of Prostate for External Beam Radiation Therapy," Annual Summary Prepared for U.S. Army Medical Research and Materiel Command, Fort Detrick MD, Award No. W81XWH-08-1-0127 (Mar. 2009).

XinRay Systems, "Products and Technology: Distributed X-Ray Source Technology," 2-page document, www.xinraysystems.com (undated).

Yang, G, et. al., "Stationary Digital Breast Tomosynthesis System With a Multi-Beam Field Emission X-Ray Source Array," Medical Imaging 2008: Physics of Medical Imaging, Proc. SPIE 6913, 69131A (2008).

Beavis "Is tomotherapy the future of IMRT?", The British J. of Radiology 77, pp. 285-295 (2004).

Court et al., "Evaluation of mechanical precision and alignment uncertainties for an itegrated CT/LINAC system", Med. Phys. vol. 30, No. 6, pp. 1198-1210 (2003).

Jaffray et al. "Flat-panel cone-beam computed tomography for image-guided radiation therapy", Int. J. Rad. Oncology Biol. Phys. vol. 53, No. 5, pp. 1337-1349 (2002).

Kuriyama et al., "A new irradiation unit constructed of self-moving gantry-CT and LINAC", Int. J. Rad. Oncology Biol. Phys. vol. 55, No. 2, pp. 428-435 (2003).

Mackie et al., "Image guidance for precise conformal radiogtherapy", Int. J. Radiation Oncology Biol. Phys. vol. 56, No. 1, pp. 89-105 (2003).

Raaymakers et al., "Integrating a MRI scanner with a 6 MV radiotherapy accelerator: dose deposition in a transverse magnetic field", Phys. Med. Biol. vol. 49, pp. 4109-1418 (2004).

Jematsu et al., "A dual computed tomography linear accelerator unit for stereotactic radiation therapy: a new approach without cranially fixated stereotactic frames", Int. J. Rad. Oncology Biol. Phys. vol. 35, No. 3, pp. 587-592 (1996).

\* cited by examiner

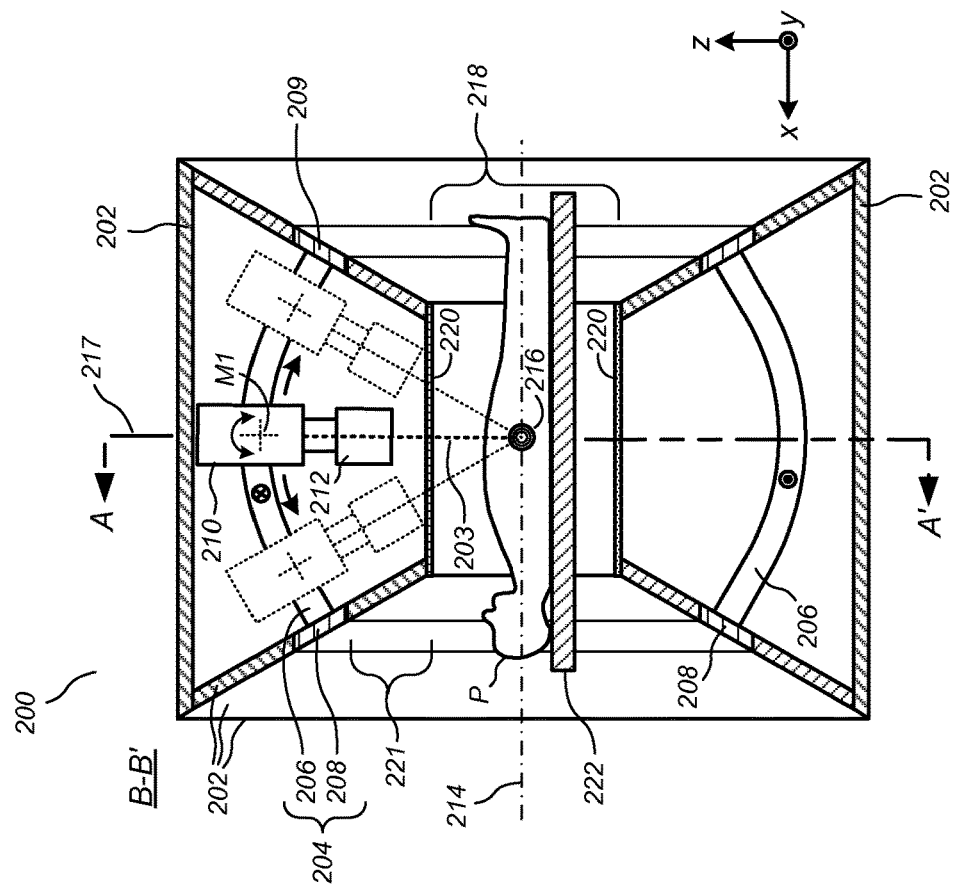
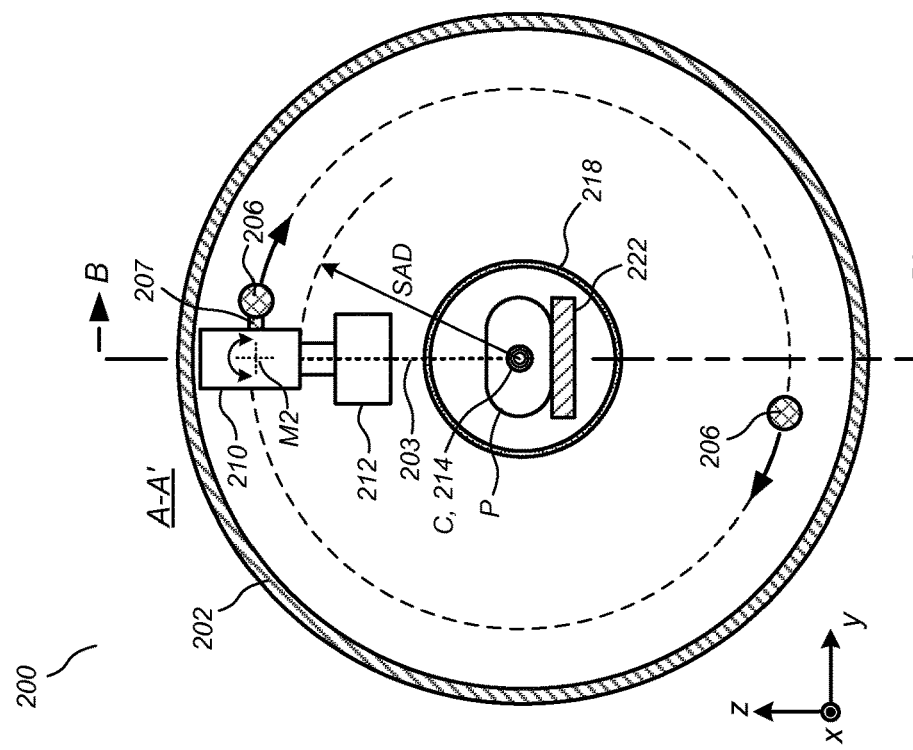
FIG. 2B
FIG. 2A

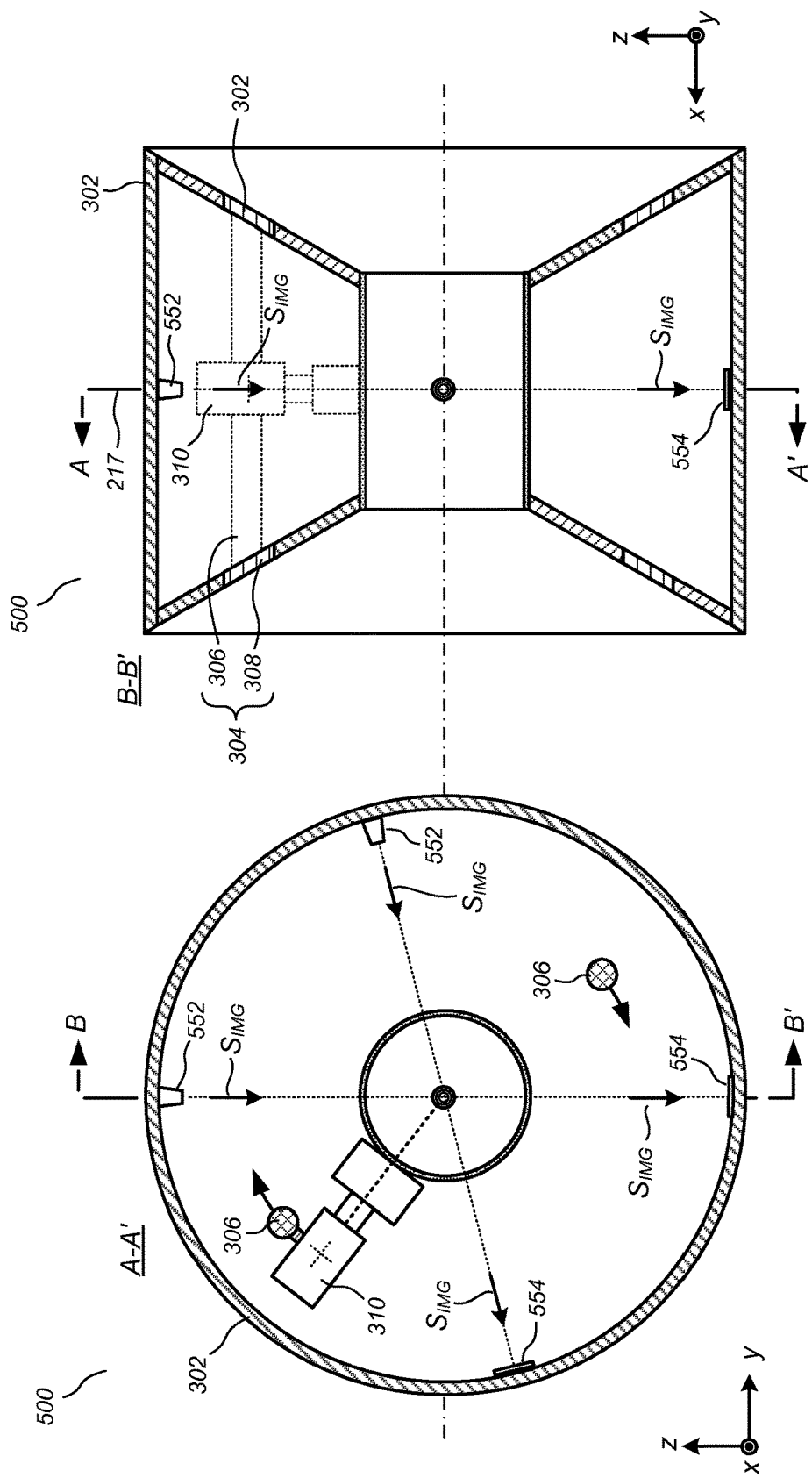

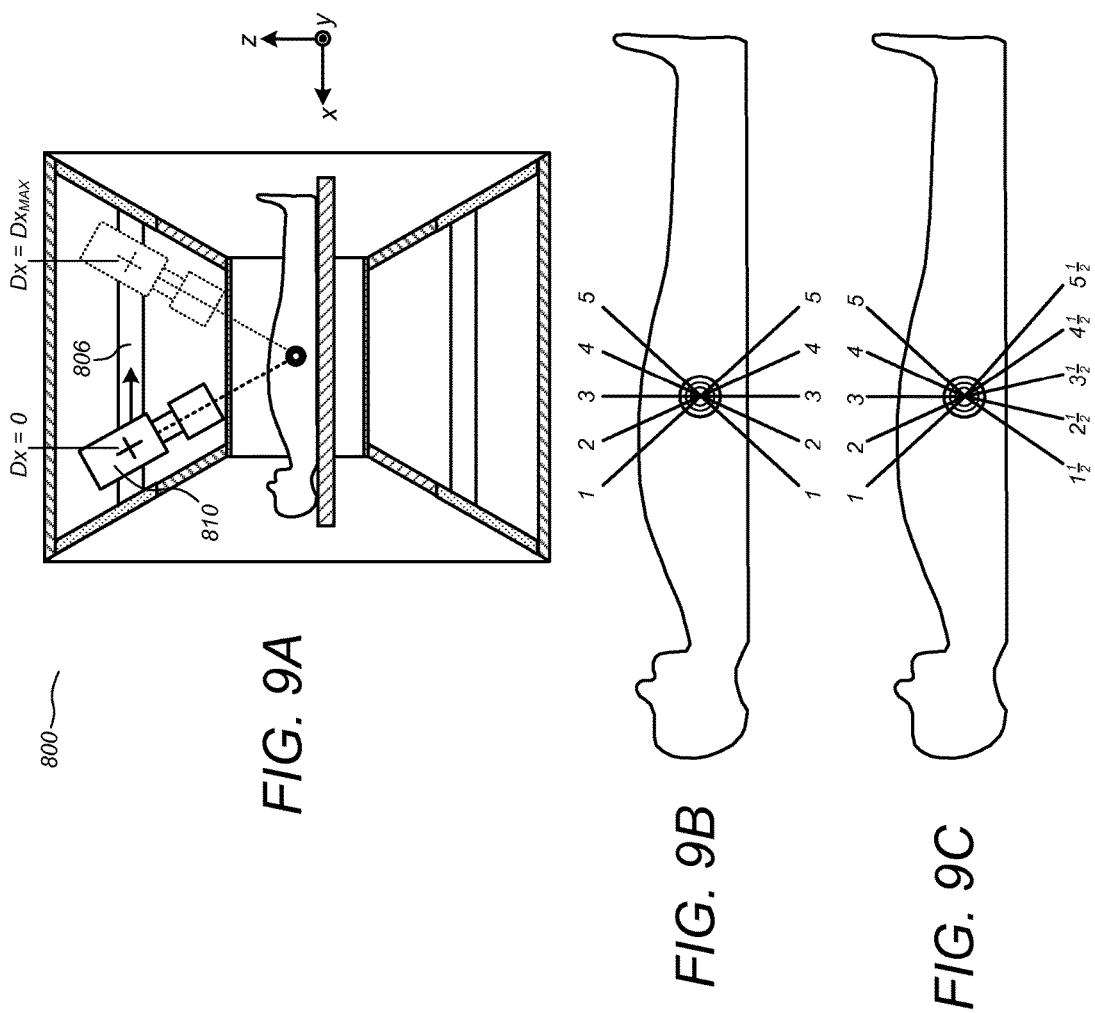

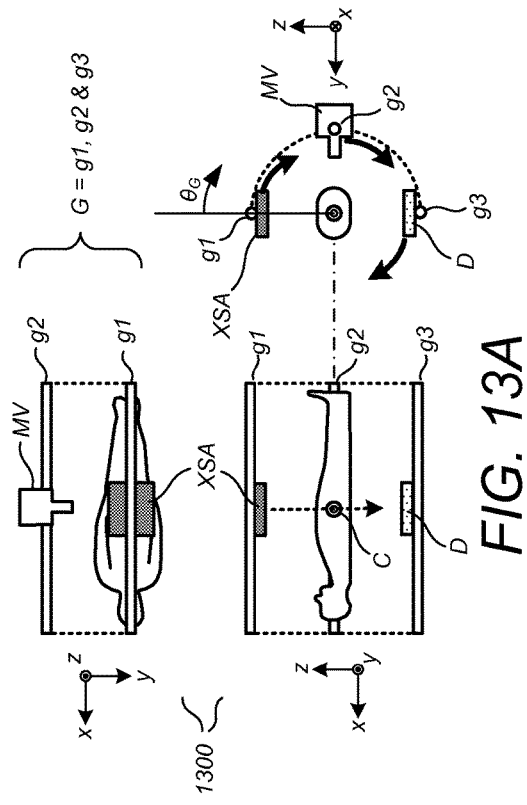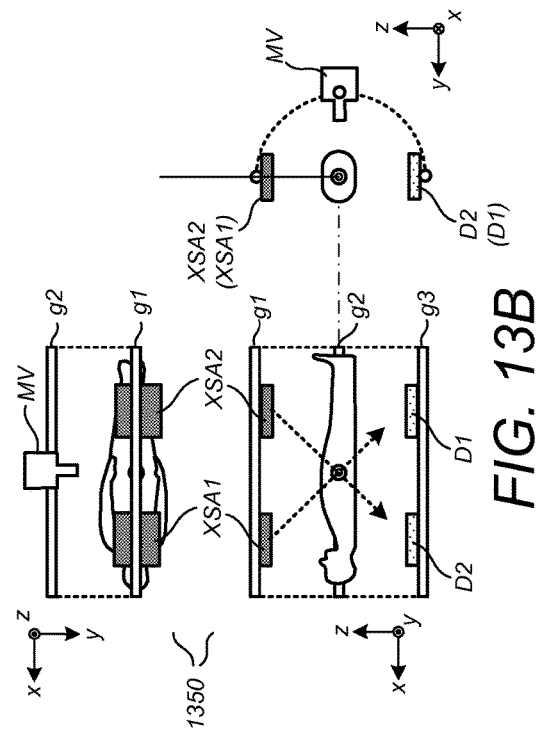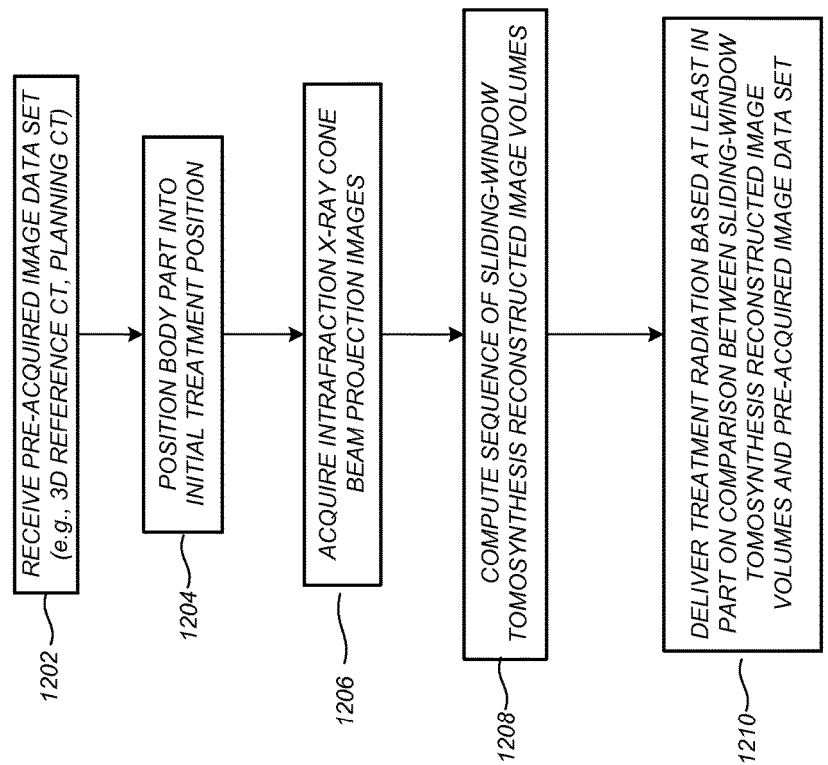

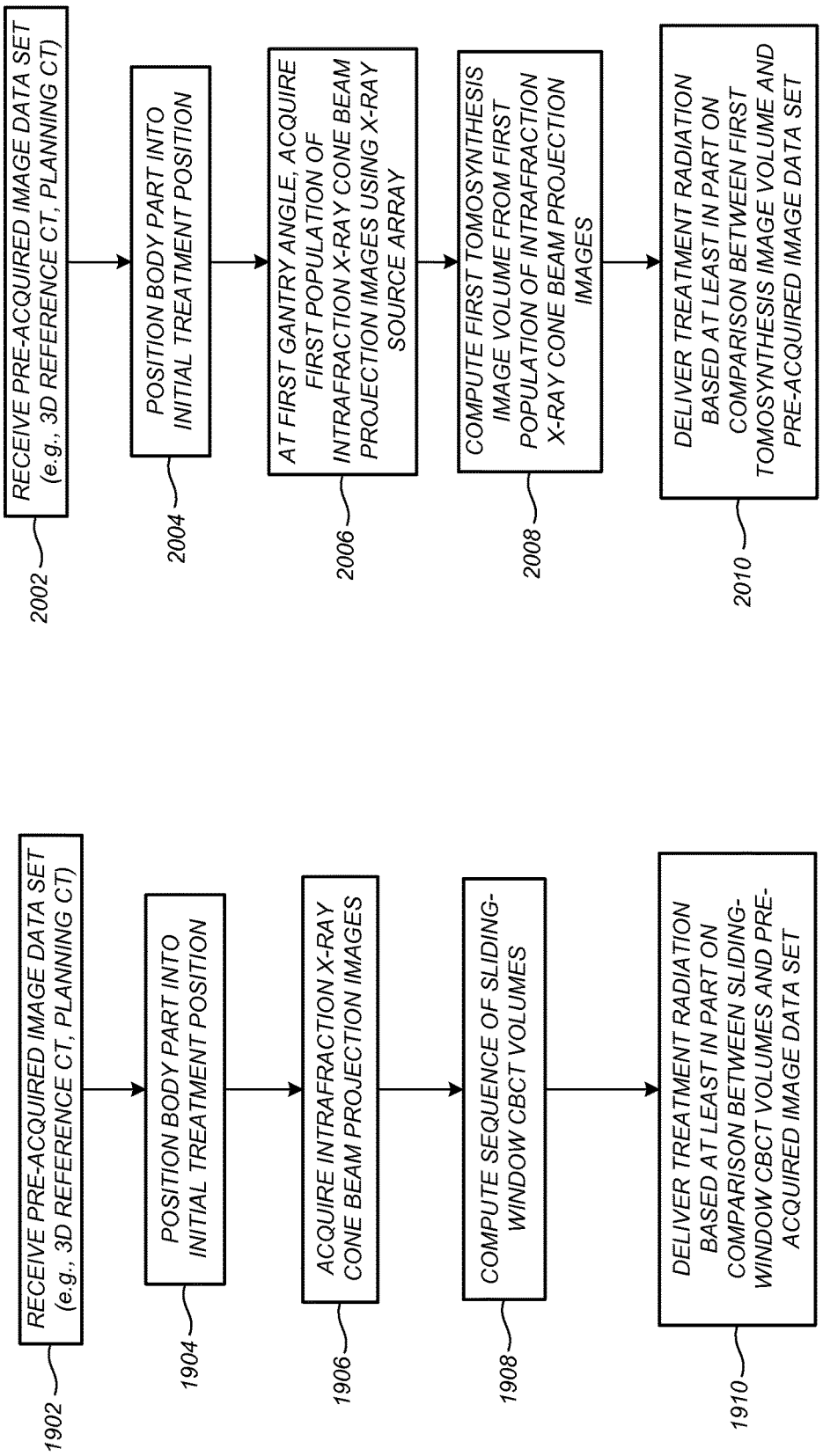

GANTRY IMAGE GUIDED RADIOTHERAPY SYSTEM AND RELATED TREATMENT DELIVERY METHODS

CROSS-REFERENCE TO RELATED APPLICATIONS

This application is a continuation of U.S. patent application Ser. No. 15/078,553, filed Mar. 23, 2016, which is a divisional application of U.S. patent application Ser. No. 14/548,095, filed on Nov. 19, 2014, which is a divisional application of U.S. patent application Ser. No. 13/033,584, filed on Feb. 23, 2011, now U.S. Pat. No. 8,934,605, issued on Jan. 13, 2015, which claims the benefit of U.S. Provisional Ser. No. 61/307,847 filed Feb. 24, 2010, and U.S. Provisional Ser. No. 61/371,732 filed Aug. 8, 2010, each of which is incorporated by reference herein. The subject matter of this patent specification is also related to the subject matter of the following commonly assigned applications, each of which is incorporated by reference herein: International Application Ser. No. PCT/US11/25936 filed Feb. 23, 2011; U.S. Provisional Ser. No. 61/352,637 filed Jun. 8, 2010; U.S. Provisional Ser. No. 61/371,733 filed Aug. 8, 2010; U.S. Provisional Ser. No. 61/371,737 filed Aug. 8, 2010; and U.S. Provisional Ser. No. 61/371,737 filed Jan. 20, 2011.

FIELD

This patent specification relates to the use of radiation for medical treatment purposes. More particularly, this provisional patent specification relates to radiation treatment systems.

BACKGROUND

Pathological anatomies such as tumors and lesions can be treated with an invasive procedure, such as surgery, which can be harmful and full of risks for the patient. A non-invasive method to treat a pathological anatomy (e.g., tumor, lesion, vascular malformation, nerve disorder, etc.) is external beam radiation therapy, which typically uses a therapeutic radiation source, such as a linear accelerator (LINAC), to generate radiation beams, such as x-rays. In one type of external beam radiation therapy, a therapeutic radiation source directs a sequence of x-ray beams at a tumor site from multiple co-planar angles, with the patient positioned so the tumor is at the center of rotation (isocenter) of the beam. As the angle of the therapeutic radiation source changes, every beam passes through the tumor site, but passes through a different area of healthy tissue on its way to and from the tumor. As a result, the cumulative radiation dose at the tumor is high and that to healthy tissue is relatively low.

The term "radiosurgery" refers to a procedure in which radiation is applied to a target region at doses sufficient to necrotize a pathology in fewer treatment sessions or fractions than with delivery of lower doses per fraction in a larger number of fractions. Radiosurgery is typically characterized, as distinguished from radiotherapy, by relatively high radiation doses per fraction (e.g., 500-2000 centiGray), extended treatment times per fraction (e.g., 30-60 minutes per treatment), and hypo-fractionation (e.g., one to five fractions or treatment days). Radiotherapy is typically characterized by a low dose per fraction (e.g., 100-200 centiGray), shorter fraction times (e.g., 10 to 30 minutes per treatment) and hyper-fractionation (e.g., 30 to 45 fractions).

For convenience, the term "radiation treatment" is used herein to mean radiosurgery and/or radiotherapy unless otherwise noted.

Image-guided radiation therapy (IGRT) systems include gantry-based systems and robotic arm-based systems. In gantry-based systems, a gantry rotates the therapeutic radiation source around an axis passing through the isocenter. Gantry-based systems include C-arm gantries, in which the therapeutic radiation source is mounted, in a cantilever-like manner, over and rotates about the axis passing through the isocenter. Gantry-based systems further include ring gantries having generally toroidal shapes in which the patient's body extends through a bore of the ring/toroid, and the therapeutic radiation source is mounted on the perimeter of the ring and rotates about the axis passing through the isocenter. Traditional gantry systems (ring or C-arm) deliver therapeutic radiation in single plane (i.e., co-planar) defined by the rotational trajectory of the radiation source. Examples of C-arm systems are manufactured by Siemens of Germany and Varian Medical Systems of California. In robotic arm-based systems, the therapeutic radiation source is mounted on an articulated robotic arm that extends over and around the patient, the robotic arm being configured to provide at least five degrees of freedom. Robotic arm-based systems provide the capability to deliver therapeutic radiation from multiple out-of-plane directions, i.e., are capable of non-coplanar delivery. Accuray Incorporated of California manufactures a system with a radiation source mounted on a robotic arm for non-coplanar delivery of radiation beams.

Associated with each radiation therapy system is an imaging system to provide in-treatment images that are used to set up and, in some examples, guide the radiation delivery procedure and track in-treatment target motion. Portal imaging systems place a detector opposite the therapeutic source to image the patient for setup and in-treatment images, while other approaches utilize distinct, independent image radiation source(s) and detector(s) for the patient set-up and in-treatment images. Target or target volume tracking during treatment is accomplished by comparing in-treatment images to pre-treatment image information. Pre-treatment image information may comprise, for example, computed tomography (CT) data, cone-beam CT data, magnetic resonance imaging (MRI) data, positron emission tomography (PET) data or 3D rotational angiography (3DRA) data, and any information obtained from these imaging modalities (for example and without limitation digitally reconstructed radiographs or DRRs).

In one common scenario, the therapeutic source is a linear accelerator (LINAC) producing therapeutic radiation (which can be termed an "MV source") and the imaging system comprises one or more independent x-ray imaging sources producing relatively low intensity lower energy imaging radiation (each of which can be termed a "kV source"). In-treatment images can comprise one or more (preferably two) two-dimensional images (typically x-ray) acquired at one or more different points of view (e.g., stereoscopic x-ray images), and are compared with two-dimensional DRRs derived from the three dimensional pre-treatment image information. A DRR is a synthetic x-ray image generated by casting hypothetical x-rays through the 3D imaging data, where the direction and orientation of the hypothetical x-rays simulate the geometry of the in-treatment x-ray imaging system. The resulting DRR then has approximately the same scale and point of view as the in-treatment x-ray imaging system, and can be compared with the in-treatment x-ray images to determine the position and orientation of the target, which is then used to guide delivery of radiation to the target.

There are two general goals in radiation therapy: (i) to deliver a highly conformal dose distribution to the target volume; and (ii) to deliver treatment beams with high accuracy throughout every treatment fraction. A third goal is to accomplish the two general goals in as little time per fraction as possible. Delivering an increased conformal dose distribution requires, for example, the ability to deliver non-coplanar beams. Delivering treatment beams accurately requires the ability to track the location of the target volume intrafraction. The ability to increase delivery speed requires the ability to accurately, precisely, and quickly move the radiation source without hitting other objects in the room or the patient, or violating regulatory agency speed limitations.

One or more issues arise with respect to known radiation therapy systems that are at least partially addressed by one or more of the preferred embodiments described further hereinbelow. Generally speaking, these issues are brought about by a tension in known radiation therapy systems between mechanical stability and system versatility, a tension that becomes more pronounced as the desired use of radiation therapy expands from head-only applications to applications throughout the body, such as (without limitation) the lungs, liver, and prostate. Robot arm-based systems tend to allow for larger ranges of radiation beam angles for different body parts than ring or C-arm gantry-based systems, especially when it is desired to keep the patient couch motionless during the radiation therapy session. Accordingly, robot arm-based systems generally tend to allow for more versatility in the kinds of therapy plans that may be available to the patient in comparison to C-arm and ring gantry-based systems. Further in view of the very heavy nature of most therapeutic radiations sources, which can weigh hundreds of kilograms, systems based on mounting of the therapeutic radiation source on a C-arm gantry suffer from undesired in-treatment deformation of the mount structures, which deformation is difficult to model or predict and leads to beam delivery errors and/or increased therapy planning margins due to the inability to precisely and accurately identify where the beam is pointed in three-dimensional space.

Ring gantry-based systems, on the other hand, tend to exhibit relatively high mechanical stability, i.e., less of the deformation problems exhibited by C-arm gantry-based systems, and thus can reproducibly and accurately position the radiation source, including doing so at relatively high mechanical drive speeds. However, as discussed above, gantry-based systems (like C-arm systems) tend to provide a lesser range of achievable angles for the introduction of therapeutic radiation into different body parts and, therefore, provide a narrower array of radiation treatment options as compared to robot arm-based systems.

X-ray tomosynthesis refers to the process of acquiring a number of two-dimensional x-ray projection images of a target volume using x-rays that are incident upon the target volume at a respective number of different angles, followed by the mathematical processing of the two-dimensional x-ray projection images to yield a set of one or more tomosynthesis reconstructed images representative of one or more respective slices of the target volume, wherein the number of x-ray projection images is less than that in a set that would be required for CT image reconstruction, and/or the number or range of incident radiation angles is less than would be used in a CT imaging procedure. Commonly, a plurality of tomosynthesis reconstructed images are generated, each being representative of a different slice of the target volume, and therefore a set of tomosynthesis reconstructed images is sometimes referred to as a tomosynthesis volume. As used herein, the term tomosynthesis projection image refers to one of the two-dimensional x-ray projection images acquired during the tomosynthesis imaging process.

For purposes of the above terminology, for some preferred embodiments, a set of images that is required for CT image reconstruction is considered to include images (e.g., 300 or more) generated over a range of incident angles that is 180 degrees plus the fan beam angle. For some preferred embodiments, the x-ray projection images for constructing a tomosynthesis image are taken over an angular range between 1 degree and an angular range value that is less than that needed for a complete projection set for CT imaging (e.g., 180 degrees plus the fan angle), wherein the number of projection images generated in this range is a value that is between 2 and 1000. In other preferred embodiments, the x-ray projection images for constructing a tomosynthesis image are taken over an angular range of between 5 degrees and 45 degrees, wherein the number of projection images generated in this range is between 5 and 100.

X-ray tomosynthesis has been proposed as an in-treatment kV imaging modality for use in conjunction with radiation treatment systems. In U.S. Pat. No. 7,532,705B2 it is proposed to process the three-dimensional pre-treatment image information (e.g., a planning CT image volume) to generate digital tomosynthesis (DTS) reference image data of a target located within or on a patient, such as by simulating x-ray cone-beam projections through the planning CT image volume. Subsequently, with the patient on the treatment bed, DTS verification images are generated by acquiring a number of x-ray cone beam images at different angles. Target localization is then performed by comparing landmarks, such as bony structures, soft-tissue anatomy, implanted targets, and skin contours in the DTS reference image data and DTS verification image data. In U.S. Pat. No. 7,711,087B2 it is proposed to acquire tomosynthesis image data during a treatment session. For purposes of movement tracking during the treatment session, tomosynthesis reconstructed slices are processed directly in conjunction with reference CT data in a process that searches for a tomosynthesis reconstructed image that best matches a selected reference CT slice. The identity of the particular tomosynthesis reconstructed image that yields a maximum degree of match, together with the amount of spatial offset required for that tomosynthesis reconstructed image to achieve the peak match, is used to localize the target in three-dimensional space. The commonly assigned U.S. Pat. No. 6,778,850, which is incorporated by reference herein, also discloses the use of x-ray tomosynthesis images (more particularly, the use of relatively low clarity intra-treatment 3D images of the target region synthesized from a plurality of 2D diagnostic images acquired at different angles) of as an in-treatment kV imaging modality.

Cone beam CT (CBCT) has also been proposed as an in-treatment imaging modality for use in conjunction with radiation treatment systems, in some cases as a kV imaging modality and in other cases as an MV (portal) imaging modality. Whereas conventional CT imaging reconstructs 2D slices from 1D projections through a target volume, the 2D slices then being stacked to form a 3D volumetric image, CBCT imaging directly constructs a 3D volumetric image from 2D projections of the target volume. As known in the art, CBCT offers the ability to form a 3D image volume from a single gantry rotation (more specifically, a rotation of at least 180 degrees plus a fan beam angle) about the target volume, whereas conventional CT requires one rotation per slice (for single-row detectors) or 1/M rotations per slice (for newer quasi-linear multi-row detectors having M rows). CBCT also provides for a more isotropic spatial resolution, whereas conventional CT limits the spatial resolution in the longitudinal direction to the slice thickness. However, because conventional CT systems usually offer a substantially higher degree of collimation near their linear or quasi-linear row detectors than can usually be afforded by CBCT systems near their two-dimensional detectors, scattering noise and artifacts are more of a problem for CBCT systems than for conventional CT systems.

In U.S. Pat. No. 7,471,765B2 it is proposed to use a CBCT imaging system including a kV x-ray tube and a flat-panel imaging detector mounted on a LINAC gantry such that the kV radiation is approximately orthogonal to the MV treatment radiation from the LINAC. Prior to treatment, a CBCT planning image is acquired for treatment planning. Subsequently, before each treatment fraction, a CBCT image is acquired and compared to the CBCT pre-treatment planning image, and the results of the comparison are used to modify the treatment plan for that treatment fraction to compensate for interfraction setup errors and/or interfraction organ motion. Due to limitations in permissible gantry rotation speeds (e.g., one rotation per minute) which cause the CBCT acquisition time to be slow compared to breathing (or other physiological cycles) of the patient, a gating scheme synchronized to patient breathing (or other physiological cycles) is used during CBCT acquisition to reduce the deleterious effects of organ motion in the reconstructed images. Also due to the relatively slow CBCT acquisition time, the CBCT volume data is generally useful only for patient set-up before each treatment fraction, and not for intra-fraction motion correction.

X-ray source arrays such as field emission "cold cathode" x-ray source arrays represent a promising advance in medical imaging and offer potential advantages over conventional x-ray tube sources in several respects. A conventional x-ray tube usually comprises a tungsten, tantalum or rhenium cathode that is heated to approximately 2000° C. to cause electrons to be emitted thermionically, the free electrons then being accelerated toward an anode by a high electrical potential such as 120 kV. X-ray radiation usable for imaging is created when the thermionically generated electrons strike an anode, usually made of tungsten, molybdenum, or copper, at a focal spot of the x-ray tube, the collision causing the emission of x-ray photons. While historically being the only practical and cost-effective way to provide imaging x-ray radiation in medical imaging environments, conventional x-ray tube sources can bring about many design compromises in view of their relatively large size and weight, high operating temperatures, high power consumption, relatively modest temporal resolution (e.g., on/off switching times), and their minimal amenability to miniaturization or formation into closely spaced arrays.

As an alternative to conventional x-ray tube technology in which free electrons are generated by thermionic emission, alternative technologies have been introduced in which the free electrons are generated by field emission. In a field emission source, free electrons are emitted upon the application of a voltage to a material having a high emission density, such as certain carbon nanotube (CNT) materials. Because field emission of electrons is produced by a high electric field, no heating is necessary. Field emission sources are thus often referred to as cold cathode sources. Advantageously, the electron beams emitted by such materials may have low divergence and thus provide ease of focusing onto a focal spot. Moreover, the virtually instantaneous response of the source offers time gating capabilities that may even be on the order of nanoseconds. Because they can be made exceedingly small, field emission x-ray sources are highly amenable to formation into arrays. According to US07505562B2, which is incorporated by reference herein, devices having 1000 pixels per meter (i.e., 1000 individual x-ray sources per meter) with pulse repetition rates on the order of 10 MHz can be envisioned using technology within the current state of the art.

As used herein, the term x-ray source array refers to a source of x-rays comprising a plurality of spatially distinct, electronically activatable x-ray emitters or emission spots (focal spots) that are addressable on at least one of an individual and groupwise basis. Although most x-ray source arrays suitable for use with one or more of the preferred embodiments will commonly be of the field emission "cold cathode" type, the scope of the present teachings is not so limited. By way of example, other types of x-ray source arrays that may be suitable for use with one or more of the preferred embodiments include scanning-beam array X-ray sources in which an electron beam digitally scans across a tungsten transmission target thirty times per second, sequentially producing ten thousand individually collimated X-ray beams, as reported by Triple Ring Technologies, Inc., of Newark, Calif.

X-ray source arrays have been proposed for use in kV imaging systems associated with radiation treatment systems, such as in US20090296886A1. However, it is believed that substantial advances in the configuration, operation, and/or manner of integration of x-ray source arrays into IGRT systems, such as those provided by one or more of the preferred embodiments herein, are needed in order to achieve clinical practicality, effectiveness, and market acceptance. It is to be appreciated the although particularly advantageous in the context of IGRT systems, one or more of the preferred embodiments is also applicable to a wide variety of other medical imaging applications outside the realm of image-guided radiation treatment.

More generally, one or more issues arises with respect to known medical imaging and/or radiation treatment systems that is at least partially addressed by one or more of the preferred embodiments described further hereinbelow. Other issues arise as would be apparent to a person skilled in the art in view of the present teachings.

SUMMARY

Provided according to one preferred embodiment is a method for image guided radiation treatment (IGRT) of a body part, comprising providing an IGRT apparatus including a rotatable gantry structure, a radiation treatment head, and a treatment guidance imaging system including a first x-ray cone beam imaging source mounted to and rotatable with the rotatable gantry structure, the treatment guidance imaging system further including a first imaging detector. A pre-acquired image data set of the body part acquired in a reference frame generally independent of a reference frame of the IGRT apparatus is received. During a patient setup interval, the body part is positioned into an initial treatment position relative to the IGRT apparatus, the initial treatment position being along an axis of rotation of the rotatable gantry structure. The rotatable gantry structure is rotated through a range of gantry angles. Subsequent to the patient setup interval, the first x-ray cone beam imaging source and the first imaging detector are operated to acquire a first population of x-ray cone beam projection images of the body part for a respective first population of gantry angles and acquisition times. The first population of x-ray cone beam projection images is processed to compute therefrom a time sequence of sliding-window tomosynthesis reconstructed image volumes characterized in that each subsequent member of the time sequence is computed using at least one same x-ray cone beam projection image as used in computing at least one previous member of the time sequence. The radiation treatment head is operated to deliver treatment radiation to the body part based at least in part on a comparison between each of the time sequence of sliding-window tomosynthesis reconstructed image volumes and the pre-acquired image data set.

Provided according to another preferred embodiment is a method for IGRT of a body part, comprising providing an IGRT apparatus including a rotatable gantry structure, a radiation treatment head, and a treatment guidance imaging system including a first x-ray cone beam imaging source mounted to and rotatable with the rotatable gantry structure, the treatment guidance imaging system further including a first imaging detector. A pre-acquired image data set of the body part acquired in a reference frame generally independent of a reference frame of the IGRT apparatus is received. During a patient setup interval, the body part is positioned into an initial treatment position relative to the IGRT apparatus, the initial treatment position being along an axis of rotation of the rotatable gantry structure. The rotatable gantry structure is rotated through a range of gantry angles greater than 180 degrees plus a fan beam angle of the first x-ray cone beam imaging source. Subsequent to the patient setup interval, the first x-ray cone beam imaging source and the first imaging detector are operated to acquire a first population of x-ray cone beam projection images of the body part for a respective first population of gantry angles and acquisition times. The first population of x-ray cone beam projection images is processed to compute therefrom a time sequence of sliding-window cone beam CT (CBCT) volumes characterized in that each subsequent member of the time sequence is computed using at least one same x-ray cone beam projection image as used in computing at least one previous member of the time sequence. The radiation treatment head is operated to deliver treatment radiation to the body part based at least in part on a comparison between each of the time sequence of sliding-window CBCT volumes and the pre-acquired image data set.

Provided according to another preferred embodiment is a method for IGRT of a body part, comprising providing an IGRT apparatus having a rotatable gantry structure, a radiation treatment head, and a treatment guidance imaging system including a first x-ray source array mounted to and rotatable with the rotatable gantry structure. The first x-ray source array has a number of x-ray sources positioned thereacross. The treatment guidance imaging system further including a first digital detector array. A pre-acquired image data set of the body part acquired in a reference frame generally independent of a reference frame of the IGRT apparatus is received. During a patient setup interval, the body part is positioned into an initial treatment position relative to the IGRT apparatus, the initial treatment position being along an axis of rotation of said rotatable gantry structure. The rotatable gantry structure is rotated through a range of gantry angles including a first gantry angle. Subsequent to the patient setup interval and with the rotatable gantry structure at the first gantry angle, the first x-ray source array and the first digital detector array are operated to acquire a first population of x-ray cone beam projection images of the body part. The first population of x-ray cone beam projection images are processed to compute therefrom a first tomosynthesis image volume. The radiation treatment head is operated to deliver treatment radiation to the body part based at least in part on a comparison between the first tomosynthesis image volume and the pre-acquired image data set.

Provided according to one or more preferred embodiments are systems, methods, and related computer program products for image-guided radiation treatment (IGRT), including an image-guided radiation therapy (IGRT) system that provides both high mechanical stability and radiation delivery and target tracking versatility. The IGRT system is robust against deformation even in cases of relatively swift movement of its therapeutic radiation source, while at the same time providing for a wide range of achievable angles for the introduction of therapeutic radiation into different body parts and providing for a wide range of imaging options for locating and tracking a target region. Therefore, IGRT systems according to one or more of the preferred embodiments provide for a wider array of radiation treatment options in relatively faster treatment times. In one or more preferred embodiments, the IGRT system further includes a highly versatile yet stable in-therapy imaging system for further enhancing overall system adaptability, precision, and performance. In other preferred embodiments, related methods for radiation treatment delivery are provided, including a method for conical non-coplanar rotational arc therapy and cono-helical non-coplanar rotational arc therapy.

Further provided according to one or more preferred embodiments are methods for intra-fraction target tracking in a gantry-style IGRT system, the methods being based on comparisons between a pre-acquired planning image and intrafraction x-ray tomosynthesis images and/or intrafraction cone beam CT (CBCT) images. The intrafraction tomosynthesis images and/or CBCT images, which can be acquired using single x-ray point sources or x-ray source arrays, such x-ray sources optionally being provided in stereoscopic and/or dual-energy or multi-energy configurations, can be compared with the pre-acquired planning image in accordance with one or more preferred embodiments that provide for one or more of streamlined intrafraction computation, reduced patient x-ray dose, and reduced treatment delivery margins, as is described further hereinbelow.

BRIEF DESCRIPTION OF THE DRAWINGS

FIGS. 2A-2B illustrate axial and side cut-away views, respectively, of an image-guided radiation treatment (IGRT) system according to a preferred embodiment;

FIGS. 5A-5B illustrate axial and side cut-away views, respectively, of an IGRT system according to a preferred embodiment;

FIGS. 9A-9C illustrate conical non-coplanar rotational arc therapy and cono-helical rotational arc therapy using an IGRT system according to a preferred embodiment;

FIG. 12 illustrates image guided radiation treatment according to a preferred embodiment;

FIGS. 13A-13B each illustrate front, top, and axial views of an IGRT system including one or more x-ray source arrays according to a preferred embodiment;

FIGS. 18-20 each illustrate image guided radiation treatment according to one or more preferred embodiments.

DETAILED DESCRIPTION

Figure 1:
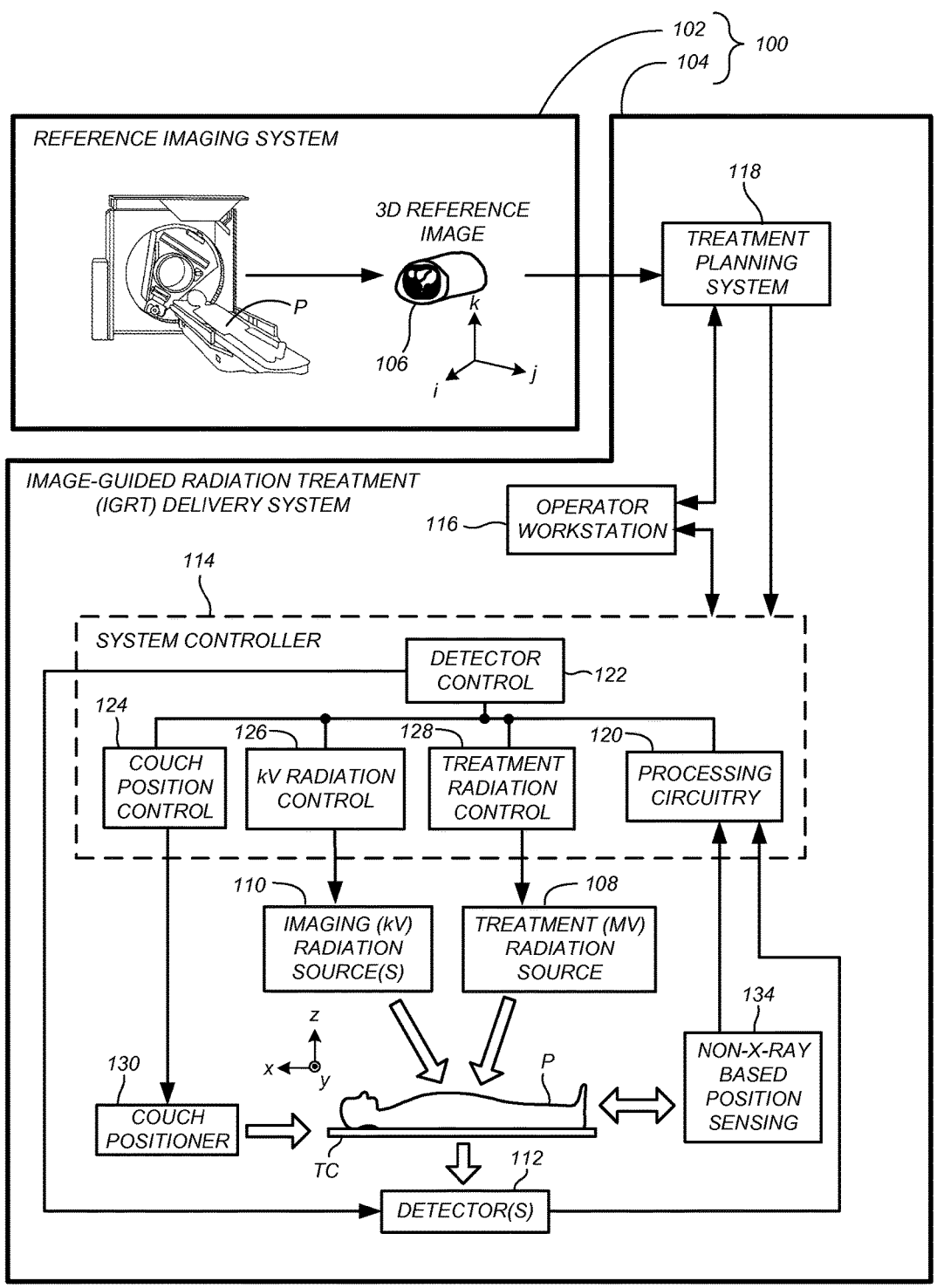
FIG. 1 illustrates a radiation treatment environment according to a preferred embodiment.

FIG. 1 illustrates a radiation treatment environment 100 within which one or more of the preferred embodiments is advantageously applied. The radiation treatment environment 100 includes a reference imaging system 102 and an IGRT system 104. Reference imaging system 102 usually comprises a high precision volumetric imaging system such as a computed tomography (CT) system or a nuclear magnetic resonance imaging (MRI) system. In view of cost and workflow considerations in many clinical environments, the reference imaging system 102 is often a general purpose tool used for a variety of different purposes in the clinic or hospital environment, and is not specifically dedicated to the IGRT system 104. Rather, the reference imaging system 102 is often located in its own separate room or vault and is purchased, installed, and/or maintained on a separate and more generalized basis than the IGRT system 104. Accordingly, for the example of FIG. 1, the reference imaging system 102 is illustrated as being distinct from the IGRT system 104. Notably, for other radiation treatment environments that are not outside the scope of the present teachings, the reference imaging system 102 can be considered as an integral component of the IGRT system 104.

IGRT system 104 comprises a radiation treatment (MV) source 108 that selectively applies high-energy x-ray treatment radiation to a target volume of a patient P positioned on a treatment couch TC. The MV source 108 applies the treatment radiation under the control of a system controller 114, and more particularly a treatment radiation control subsystem 128 thereof. System controller 114 further comprises processing circuitry 120, a detector controller 122, a couch position controller 124, and a kV radiation controller 126 each programmed and configured to achieve one or more of the functionalities described further herein. One or more imaging (kV) radiation sources 110 selectively emit relatively low-energy x-ray imaging radiation under the control of kV radiation controller 126, the imaging radiation being captured by one or more imaging detectors 112. In alternative preferred embodiments, one or more of the imaging detectors 112 can be a so-called portal imaging detector that captures high-energy x-ray treatment radiation from MV source 108 that has propagated through the target volume.

For one preferred embodiment, the kV imaging radiation sources 110 include both a two-dimensional stereotactic x-ray imaging system and a tomosynthesis imaging system. For other preferred embodiments, only a two-dimensional stereotactic x-ray imaging system is provided, while for still other preferred embodiments only a tomosynthesis imaging system is provided. Preferably, each of the stereotactic x-ray imaging system and the tomosynthesis imaging system are characterized by either (a) a fixed, predetermined, nonmoving geometry relative to the (x, y, z) coordinate system of the treatment room, or (b) a precisely measurable and/or precisely determinable geometry relative to the (x, y, z) coordinate system of the treatment room in the event they are dynamically moveable. The MV radiation source 108 should also, of course, have a precisely measurable and/or precisely determinable geometry relative to the (x, y, z) coordinate system of the treatment room.

A couch positioner 130 is actuated by the couch position controller 124 to position the couch TC. A non-x-ray based position sensing system 134 senses position and/or movement of external marker(s) strategically affixed to the patient, and/or senses position and/or movement of the patient skin surface itself, using one or more methods that do not involve ionizing radiation, such as optically based or ultrasonically based methods. In one example, IGRT system 104 can be similar to a CYBERKNIFE® robotic radiosurgery system available from Accuray Incorporated of Sunnyvale, Calif., and the position sensing system 134 can be similar to relevant sensing components of the Accuray Incorporated SYNCHRONY® respiratory tracking system. IGRT system 104 further includes an operator workstation 116 and a treatment planning system 118.

In common clinical practice, treatment planning is performed on a pre-acquired treatment planning image 106 generated by the reference imaging system 102. The pre-acquired treatment planning image 106 is often a high resolution three-dimensional CT image acquired substantially in advance (e.g., one to two days in advance) of the one or more radiation treatment fractions that the patient will undergo. As indicated in FIG. 1 by the illustration of an (i, j, k) coordinate system for the pre-acquired treatment planning image 106, which is in contrast to the (x, y, z) treatment room coordinate system illustrated for the treatment room of the IGRT system 104, there is generally no pre-existing or intrinsic alignment or registration between the treatment planning image 106 coordinate system and the treatment room coordinate system. During the treatment planning process, a physician establishes a coordinate system (e.g., i, j, k in treatment planning image 106) within the treatment planning image, which may also be referred to herein as the planning image coordinate system or planning image reference frame. A radiation treatment plan is developed in the planning image coordinate system that dictates the various orientations, sizes, durations, etc., of the high-energy treatment radiation beams to be applied by the MV source 108 during each treatment fraction. Accurate delivery of therapeutic radiation to a target requires aligning the planning image coordinate system with the treatment room coordinate system, as the entire delivery and tracking system (if present) is calibrated to the treatment room coordinate system. It will be appreciated that this alignment does not need to be exact and further appreciated that couch adjustment or beam delivery adjustment can be used to account for offsets in the alignment between the two coordinate systems.

Thus, immediately prior to each treatment fraction, under a precise image guidance of the kV imaging radiation sources 110, according to one or more of the embodiments described further hereinbelow, the patient is physically positioned such that the planning image coordinate system (defined, for example and not by way of limitation, by a physician while creating a treatment plan on a CT image or planning image) is positioned into an initial alignment with the treatment room coordinate system, hereinafter termed an initial treatment alignment or initial treatment position. This alignment is commonly referred to as patient set up. Depending on the location of the target volume, the target volume can vary in position and orientation and/or can undergo volumetric deformations due to patient movement and/or physiological cycles such as respiration. As used herein, the term in-treatment alignment variation or in-treatment position variation is used to refer to the variations in position, orientation, and/or volumetric shape by which the current state of the target volume differs from the initial treatment alignment. By virtue of a known relationship between the treatment planning coordinate system and the treatment room coordinate system, the term in-treatment alignment variation can also be used to refer to the variations in position, orientation, or volumetric shape by which the current state of the target volume differs from that in the treatment planning coordinate system. More generally, the term initial treatment alignment or initial treatment position refers herein to the particular physical pose or disposition (including position, orientation and volumetric shape) of the body part of the patient upon patient setup at the outset of the treatment fraction.

A non x-ray based position sensing system 134 may also be provided. This non x-ray based position sensing system 134 may include, by way of example and without limitation, external markers affixed in some manner to a patient's chest which move in response to respiration (other mechanisms for monitoring respiration may be used), and include a mono or stereoscopic x-ray imaging system, which as described above can precisely determine target location. System 134 correlates motion of the external markers with target motion, as determined from (for example) the mono or stereoscopic x-ray projections. Non x-ray based position sensing system 134, therefore, permits system controller 114 to monitor external marker motion, use the correlation model to precisely predict where the target will be located in real time (e.g., ~60 Hz), and direct the treatment beam to the target. As treatment of the moving target progresses additional x-ray images may be obtained and used to verify and update the correlation model.

According to a preferred embodiment, system controller 114 including processing circuitry 120 is configured and programmed to receive information from the non-x-ray based position sensing system 134 and the imaging detector(s) 112 or just from the imaging detector(s) 112 when treating a relatively stationary target volume (for example and without limitation a brain, spine or prostate tumor), compute an in-treatment alignment variation therefrom, and control the treatment radiation source 108 in a manner that compensates for the in-treatment alignment variation on a continual basis. In the case where the target volume moves due to respiration, the more information-rich x-ray-based data from the imaging detectors 112 is updated at a relatively slow rate compared to the breathing cycle of the patient (for example, once every 15 seconds) to maintain reasonably low x-ray imaging dose levels, the less information-rich data from the non-x-ray based position sensing system 134 can be updated in substantially real-time (for example, 30 times per second). Using methods such as those described in the commonly assigned US06501981B1, a correlation model between one or more x-ray-sensed internal target volume (with our without fiducials) and one or more non-x-ray-sensed external markers is used to ascertain the in-treatment alignment variations on a real-time basis, the correlation model being updated (corrected) at each x-ray imaging interval. Advantageously, judicious x-ray/tomosynthesis imaging source collimation strategies according to one or more of the preferred embodiments described further infra can be advantageously used to improve determination of in-treatment alignment variations or target tracking by virtue of one or more of higher x-ray/tomosynthesis imaging quality, reduced x-ray radiation dose, and higher x-ray/tomosynthesis imaging data acquisition rates.

It is to be appreciated that the use of a non-x-ray based position sensing system 134 such as the SYNCHRONY® respiratory tracking system represents an option that, while advantageous in the radiation treatment of certain tumors within the lung or chest area, is not required for radiation treatments in many other body parts, such as the prostate, spine or brain. Whereas x-ray dosage concerns provide limits on the number of kV x-ray images that should be acquired in any particular intrafraction time interval (for example, no more than one kV image every 15 seconds, every 30 seconds, or every 60 seconds), tumors within the chest area, liver or pancreas can move at substantially faster periodic rates due to respiration, therefore giving rise to the need for the non-x-ray based position sensing system 134. However, for parts in other parts of the body, such as the prostate, spine or brain, will generally experience motion on a much slower time scale, wherein the dose-limited kV x-ray imaging rate will be still be sufficiently high to effectively guide the radiation treatment. The prostate, for example, may experience movement due to an accumulation of urine in the nearby urinary bladder, an event for which one kV x-ray image every 60 seconds should be sufficient to track resultant movement. Accordingly, for the many other parts of the anatomy for which kV imaging rates are sufficient, the non-x-ray based position sensing system 134 and the associated "real time" tracking (i.e., tracking at a rate faster than the kV imaging rate) is not required.

It is to be appreciated that the exemplary radiation treatment environment of FIG. 1 is presented by way of example and not by way of limitation, that the preferred embodiments are applicable in a variety of other radiation treatment environment configurations, and that one or more of the preferred embodiments is applicable to general medical imaging environments outside the particular context of radiation treatment systems. Thus, for example, while one or more of the preferred embodiments is particularly advantageous when applied in the context of a radiation treatment environment in which the reference imaging system 102 is physically separated from, has no common coordinate system with, and/or has no other intrinsic means of volumetric image registration with the IGRT delivery system 104, the scope of the present teachings is not so limited. Rather, the one or more preferred embodiments can also be advantageously applied in the context of radiation treatment environments in which the reference imaging system is physically integral with radiation treatment delivery system or has other intrinsic linkages, such as a rail-based patient movement system, with the radiation treatment delivery system.

As used herein, "registration" of medical images refers to the determination of a mathematical relationship between corresponding anatomical or other (e.g. fiducial) features appearing in those medical images. Registration can include, but is not limited to, the determination of one or more spatial transformations that, when applied to one or both of the medical images, would cause an overlay of the corresponding anatomical features. The spatial transformations can include rigid-body transformations and/or deformable transformations and can, if the medical images are from different coordinate systems or reference frames, account for differences in those coordinate systems or reference frames. For cases in which the medical images are not acquired using the same imaging system and are not acquired at the same time, the registration process can include, but is not limited to, the determination of a first transformation that accounts for differences between the imaging modalities, imaging geometries, and/or frames of reference of the different imaging systems, together with the determination of a second transformation that accounts for underlying anatomical differences in the body part that may have taken place (e.g., positioning differences, overall movement, relative movement between different structures within the body part, overall deformations, localized deformations within the body part, and so forth) between acquisition times.

Figure 2C:
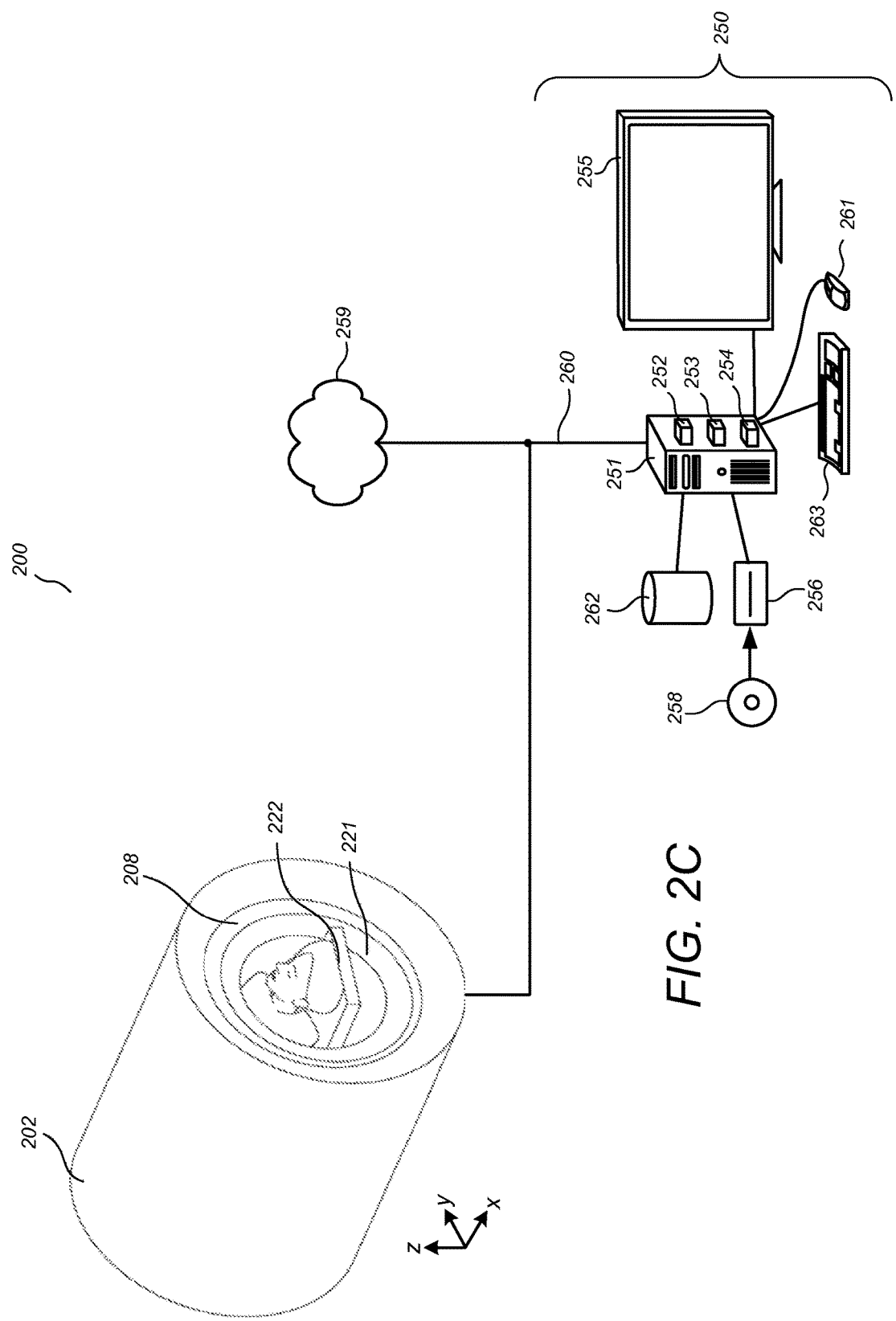
FIG. 2C illustrates a perspective view of the IGRT system of FIGS. 2A-2B and a schematic diagram of a computer system integral therewith and/or coupled thereto according to a preferred embodiment.

FIGS. 2A-2C illustrate an IGRT system 200 that is capable of carrying out the functionalities described above with respect to the IGRT system 104 of FIG. 1 according to one or more preferred embodiments. Included in FIG. 2C is a diagram of a computer system 250 integrated with the IGRT system 200, the computer system 250 being omitted from FIGS. 2A-2B for clarity of description. IGRT system 200 comprises a gantry frame 202 within which is disposed a rotatable gantry structure 204 configured to rotate around a rotation axis 214 that passes through an isocenter 216. Associated with the IGRT system 200 is an imaginary plane, termed herein a transverse isocentric plane 217, that is orthogonal to the rotation axis 214 and passes through the isocenter 216. The gantry frame 202, the isocenter 216, the rotation axis 214, and the transverse isocentric plane 217 are preferably fixed and motionless relative to a treatment vault (not shown) in which the IGRT system 200 is installed. As used herein, isocenter or machine isocenter is a physical point in a treatment room (treatment vault). A treatment center is a point within the target volume defined by a physician during treatment planning, normally based within the pretreatment CT image reference frame. For isocentric treatment the treatment center is aligned with the machine isocenter during the set up procedure described above.

The rotatable gantry structure 204 includes one or more beam members 206 that each extend between first and second ring members 208 and 209 disposed on opposite sides of the transverse isocentric plane 217. The first ring member 208 corresponds generally to a first end of the rotatable gantry structure 204 (toward the left side of FIG. 2B), while the second ring member 209 corresponds generally to a second, opposite end of the rotatable gantry structure 204 (toward the right side of FIG. 2B). The first and second ring members 208 and 209 are supported at their respective ends of the rotatable gantry structure 204 by corresponding ends of the gantry frame 202 in a manner that allows and facilitates rotation of the rotatable gantry structure 204 around the rotation axis 214 while keeping the rotation axis 214 highly stable and stationary. The skilled artisan will appreciate that any of a variety of different mechanical support schemes that allow such rotation can be used (e.g., anti-friction sleeves, slip bearings, roller bearings, etc.). The skilled artisan will appreciate that the gantry frame 202 can be made substantially thicker or otherwise reinforced at its respective ends than is indicated schematically in FIG. 2B, in accordance with the particular materials being used and other design considerations, for ensuring such mechanical stability. Without loss of generality, the rotatable gantry structure 204 contains two beam members 206 separated by 180 degrees around the rotation axis 214, which is useful (for example and without limitation) for facilitating rotational balancing (e.g. by applying appropriate balancing weights to the opposing beam members 206). The skilled artisan will appreciate that the term beam member as used herein can encompass a wide variety of different types of structural members (e.g., solid rods, hollow rods, assemblies of parallel or concentric rods, truss-type structures, etc.) that can structurally extend from one place to another and along which one or more physical items (e.g., LINACs, LINAC assemblies, imaging sources, imaging detectors, and so forth) can be fixably or movably mounted or positioned.

Movably mounted on one of the beam members 206 is a therapeutic radiation head 210, such as and without limitation a linear accelerator (LINAC) or a compact proton source, which includes thereon an end collimator 212, such as a multi-leaf collimator (MLC), and which provides a therapeutic radiation beam 203. The therapeutic radiation head 210 can alternatively be termed a radiation treatment head and is designated as such in one or more sections hereinbelow. The therapeutic radiation head 210 is mounted to the beam member 206 by a coupling device 207 that is configured and adapted to achieve the translational and rotational functionalities described further hereinbelow. The rotatable gantry structure 204 and therapeutic radiation head 210 are dimensioned so as to allow a central bore 218 to exist, that is, an opening sufficient to allow a patient P to be positioned therethrough without the possibility of being incidentally contacted by the therapeutic radiation head 210 or other mechanical components as the gantry rotates radiation head 210 about patient P. A patient couch 222 is provided for supporting the patient P, the patient couch 222 preferably being coupled to an automated patient positioning system (not shown) for moving the patient P into a therapy position and manipulating the patient with three or more degrees of freedom (e.g., three orthogonal translations, one parallel to the rotation axis 214, two orthogonal to rotation axis 214, plus optionally one or more rotations). The skilled artisan will appreciate that many couches can be used in accordance with embodiments of the present invention.

According to one preferred embodiment, a cylindrically shaped bore shield 220 is provided to line the boundary of the central bore 218. In addition to preventing unexpected movement of the patient's hands or other body part into collision with moving parts, the bore shield 220 can reduce the sense of intimidation that the patient might feel in view of the large moving parts in the device. The bore shield 220 provides the ability to maximize the rotation speed of the gantry, while still meeting all regulatory safety requirements. The bore shield 220 should be formed of a material that is substantially transparent to the therapeutic and imaging radiation, and optionally can be visibly opaque as well. Also according to a preferred embodiment, the gantry frame 202 is configured and dimensioned such that a conical tapering 221 is provided at one or both ends of the central bore 218. At a given end of the central bore 218 (e.g., the left end in FIG. 2B), the conical tapering 221 can extend from the bore opening to the ring member 208. Depending on the particular body part being treated, patient visibility into the surrounding room can be enhanced to provide a less claustrophobic experience for the patient. In combination, or alternatively, bore shield 220 could be a structural supporting cylinder or hub to which frame 202 is mechanically connected at approximately opposite ends of the supporting cylinder or hub. In such an embodiment the hub will provide additional or alternative structural support in addition to or in lieu of frame 202. In another embodiment the hub (whether or not made from radiolucent material) and/or the bore shield 220 has a longitudinal slit parallel to rotation axis 214 to allow radiation to pass therethrough unimpeded, thereby reducing the possibility of the so-called skin effect or to maximize skin sparing. As will be appreciated, the bore shield 220 could still line the structural cylinder and need not necessarily possess the slit, thereby fully closing off patient view and access to the rotating radiation source. The slit, if viewable by a patient, could be constructed so as to minimize potential access to the rotating radiation source, and the patient would likely only see the rotating radiation source when it is at or near the top of the ring pointing approximately vertically down. As will be appreciated, the hub will rotate in approximate unison with the radiation head. Stated in a different way, as an additional option, the bore shield 220 can be coupled such that it rotates with the rotatable gantry structure 204. This provides an option of leaving an open slit within the bore shield 220 through which the therapeutic radiation beam 203 can pass, which could be used to maximize skin sparing. This obscures the patient's view of most of the moving parts (indeed, unless the beam is somewhere above them they will only see the inside of the bore shield) and allows a free beam path that might be important to minimize skin dose, particularly if only a few beams are used. Optionally, to maintain moving components behind a fixed surface covering as much as possible in view of skin sparing issues, a removable cover can be provided to "plug" the slit, which would be fitted for rotational therapy treatment. For treatments using just a few (1-4) static beams, where build up is most critical but rotation speed between beams is not, then the slit is kept open. For rotational arc therapy treatments where build up is not critical (because skin dose is smeared out over so many beam directions) but rotation speed is critical, then the plug is fitted into the slit. This can be achieved manually in pre-treatment which a totally removable plug, or alternatively there is provided a mechanically sliding system on the bore shield 220 that can cover and uncover the slit under control and/or actuation of the treatment technician.

According to a preferred embodiment, the therapeutic radiation head 210 is mounted to the beam member 206 in a manner that allows and facilitates (i) translation of the therapeutic radiation head 210 along the beam member 206 (i.e., in an end-to-end manner between first ring member 208 and second ring member 209), (ii) pivoting of the therapeutic radiation head 210 around a first pivot axis M1, termed herein a primary pivot axis, and (iii) pivoting of the therapeutic radiation head 210 around a second axis M2, termed herein a secondary pivot axis, located at a right angle to M1. Preferably, the axes M1 and M2 each pass through the center of mass (CoM) of the therapeutic radiation head 210, and the center of mass lies along the axis of the therapeutic radiation beam 203 Collectively, the primary pivoting around axis M1 and the secondary pivoting around axis M2 can be considered as a gimbal or gimballing motion of the therapeutic radiation head 210. For clarity of description, the primary pivoting around axis M1 may be referenced hereinbelow by the term "M1 pivot" or "M1 pivoting," and the secondary pivoting around axis M2 may be referenced hereinbelow by the term "M2 pivot" or "M2 pivoting." Notably, the terms primary/M1 and secondary/M2 are used herein for identification purposes and are not indicative of any particular imaging-related or treatment-related relative rankings. For the preferred embodiment of FIGS. 2A-2C, the beam member 206 upon which the therapeutic radiation head 210 is mounted is concavely shaped relative to the rotation axis 214 such that the source-axis distance (SAD) remains approximately fixed for the range of translation distances of the therapeutic radiation head 210 along beam member 206. Preferably, the axes M1 and M2 pass through the center of mass (CoM) of the therapeutic radiation head, which is also coincident with the radiation source (e.g., focal spot in a LINAC). This makes treatment planning simpler and minimizes SAD variation with gimballing during tracking. Thus, there are three possibilities, each being within the scope of the present teachings, with regard to that which the axes M1 and M2 pass through: CoM of the therapeutic radiation head 210 for mechanical advantage; the axis of the therapeutic radiation source for advantage in treatment planning and providing minimal SAD variation with gimballing during tracking advantage; or both. By way of example, achieving both for a LINAC could include the use of balancing weights.

The skilled artisan will appreciate that the IGRT system 200 further includes a plurality of actuators of various types (not shown) for achieving the mechanical functionalities described hereinabove and hereinbelow in the instant disclosure. Thus, for example, the IGRT system 200 includes respective actuation devices (not shown) to achieve the rotation of the rotatable gantry structure 204 around the rotation axis 214, the axial translation of the therapeutic radiation head 210 along the beam member 206, the M1 pivoting of the therapeutic radiation head 210, and the M2 pivoting of the therapeutic radiation head 210. The IGRT system 200 further includes one or more processing and/or control units, such as may be implemented on one or more programmable computers, for controlling the various actuators and sending signals to and from the various recited radiation sources and detectors as necessary to achieve the functionalities described hereinabove and hereinbelow in the instant disclosure. In view of the present disclosure, those skilled in the art would be able to configure such actuation devices, processing and/or control units, programmable computers, etc., and operate the described IGRT systems without undue experimentation.

Included in FIG. 2C is a schematic diagram of a computer system 250 integrated with and/or coupled to the IGRT system 200 using one or more busses, networks, or other communications systems 260, including wired and/or wireless communications systems, and being capable in conjunction therewith of implementing the methods of one or more of the preferred embodiments. Methods of image guided radiation treatment in accordance with one or more of the preferred embodiments may be implemented in machine readable code (i.e., software or computer program product)

and performed on computer systems such as, but not limited to, the computer system 250, wherein a central processing unit (CPU) 251 including a microprocessor 252, random access memory 253, and nonvolatile memory 254 (e.g., electromechanical hard drive, solid state drive) is operated in conjunction with various input/output devices, such as a display monitor 255, a mouse 261, a keyboard 263, and other I/O devices 256 capable of reading and writing data and instructions from machine readable media 258 such as tape, compact disk (CD), digital versatile disk (DVD), blu-ray disk (BD), and so forth. In addition, there may be connections via the one or more busses, networks, or other communications systems 260 to other computers and devices, such as may exist on a network of such devices, e.g., the Internet 259. Software to control the image guided radiation treatment steps described herein may be implemented as a program product and stored on a tangible storage device such as the machine readable medium 258, an external nonvolatile memory device 262, or other tangible storage medium. For clarity of presentation, the computer system 250 of FIG. 2C is omitted from further drawings and/or descriptions hereinbelow. Methods for configuring and programming the computer system 250 for achieving the functionalities described herein would be apparent to a person skilled in the art in view of the present disclosure.

Advantageously, by virtue of the possibilities provided by the combination of axial translation of the therapeutic radiation head 210, M1 pivoting, and M2 pivoting, a rich variety of radiation treatment delivery plans are facilitated by the IGRT system 100, as will be discussed further infra. At the same time, by virtue of a ring-style mechanical nature of the rotatable gantry structure 204 (which could be more particularly referenced as a "barrel-style" mechanical nature), a greater degree of mechanical stability may be provided in comparison to approaches in which therapeutic radiation head support is of a cantilever-like nature. Generally speaking, in addition to positively affecting the range of achievable tilt angles (i.e., the angle between the therapeutic radiation beam 203 and the transverse isocentric plane 217 when the therapeutic radiation beam is isocentric, see FIG. 4A), increased end-to-end distance between the ring members 108 and 109 will have an impact on the mechanical stability of the device. The selection of the end-to-end distance between the ring members 108 and 109 will also have an impact on the end-to-end length of the central bore 118, which should not get too long, and the overall height of the gantry frame 202, which should not get too high so that the system may fit within most existing radiation treatment vaults.

Figure 2D:
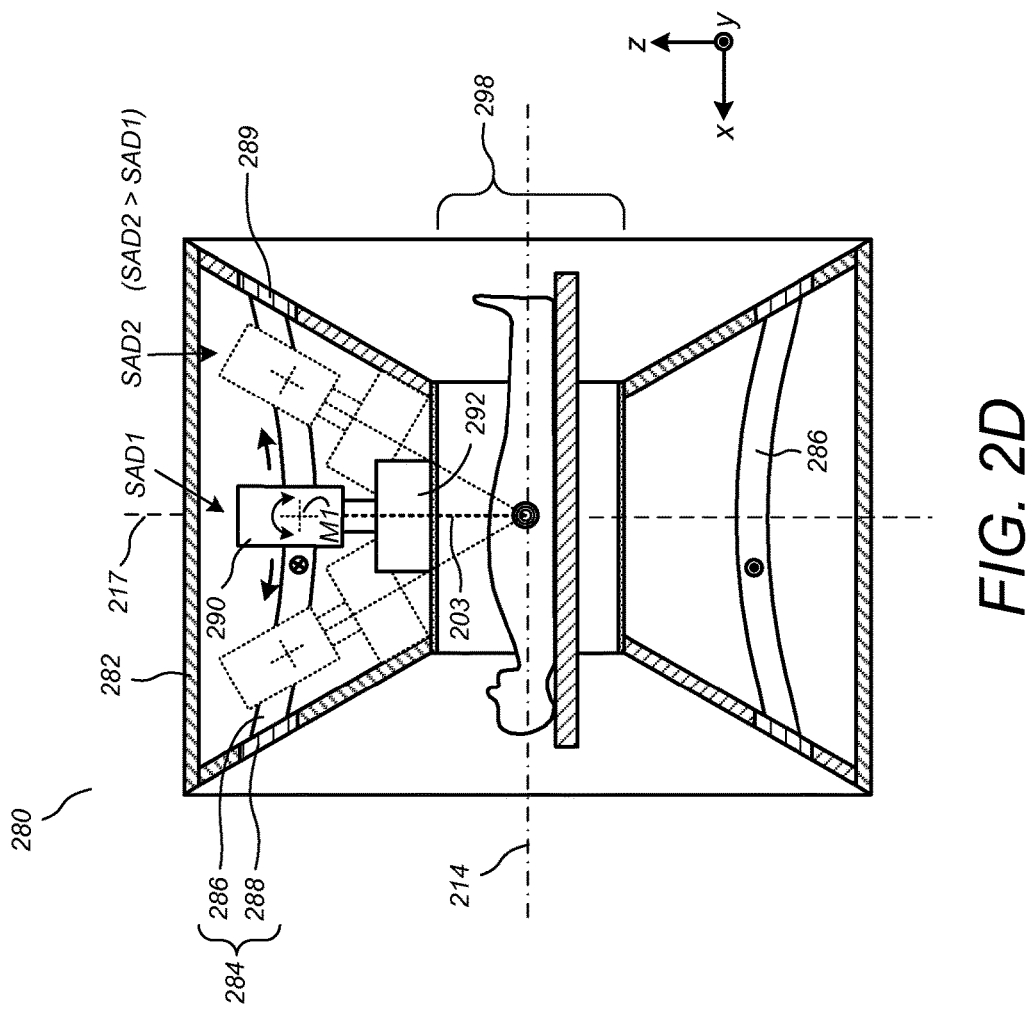
FIG. 2D illustrates a side cut-away view of an IGRT system according to a preferred embodiment.

FIG. 2D illustrates an IGRT system 280 according to another preferred embodiment, comprising a gantry frame 282, a rotatable gantry structure 284 including beam members 286 and ring members 288 and 289, and a therapeutic radiation head 290 including an end collimator 292. The IGRT system 280 is similar to the IGRT system 200 of FIGS. 2A-2C except that the beam member 286 upon which the therapeutic radiation head 290 is mounted is convexly shaped relative to the rotation axis 214. The convexity of the beam member 286 accommodates a physically larger end collimator 292, which for certain MLC designs can have a rather large width. Advantageously, the larger end collimator 292 is accommodated while also maintaining a required minimum diameter for a central bore 298, and while also providing a desirably lesser SAD as the therapeutic radiation head 290 approaches the transverse isocentric plane 217, whereas the SAD is greater near the ends of the beam member 286 in order to maintain the diameter of central bore 298.

Figure 3A:
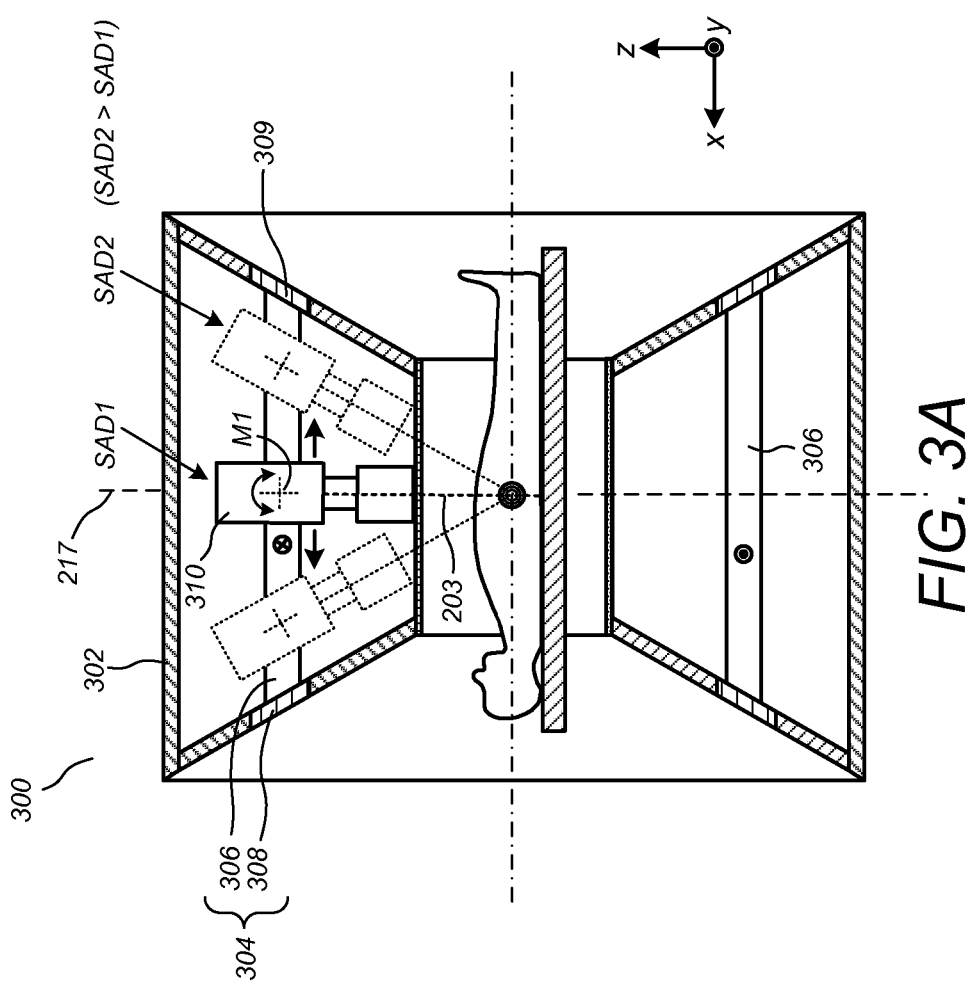
FIG. 3A illustrates a side cut-away view of an IGRT system according to a preferred embodiment.
Figure 3B:
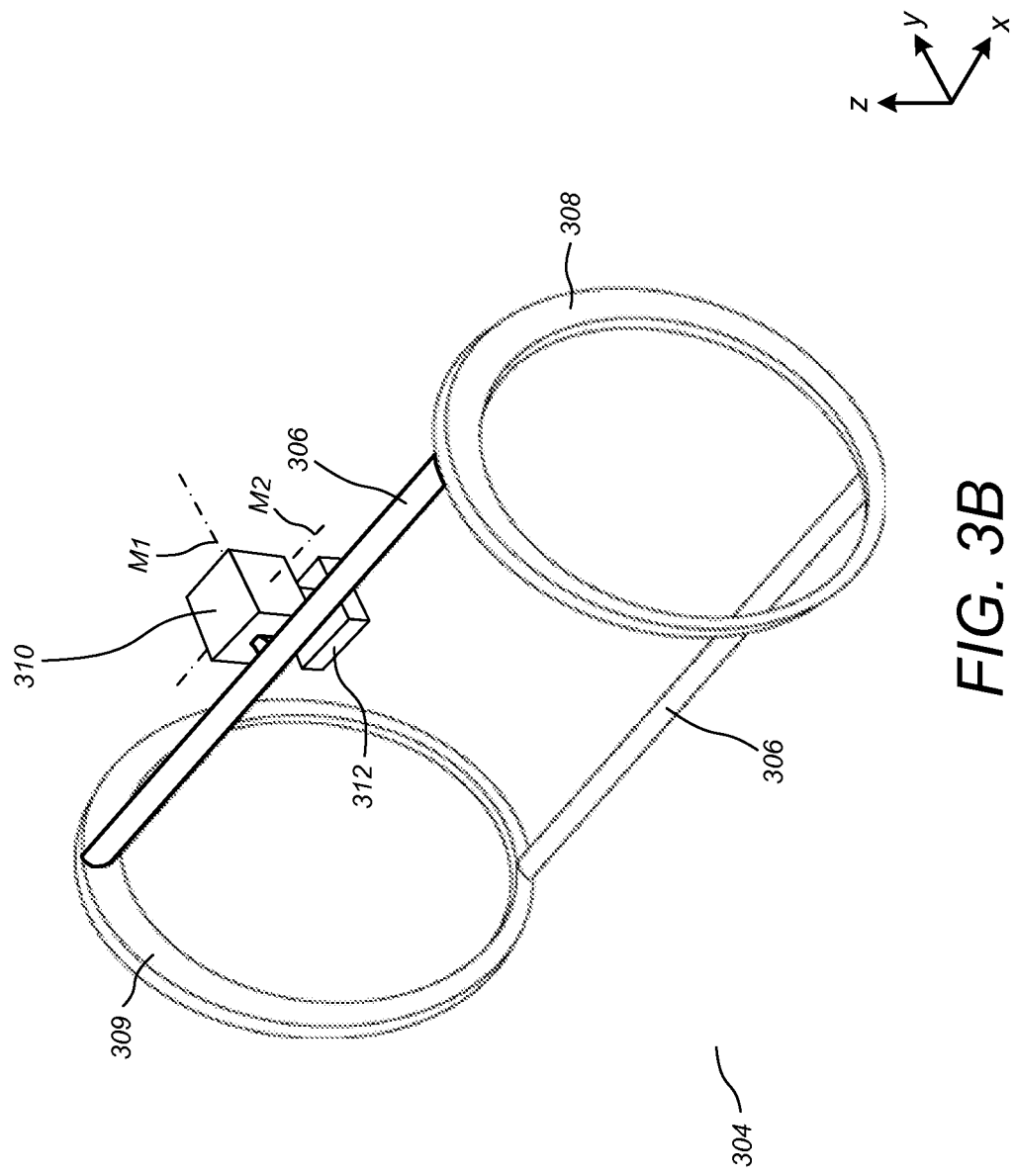
FIG. 3B illustrates a perspective view of a rotatable gantry structure of the IGRT system of FIG. 3A.

FIGS. 3A-3B illustrate an IGRT system 300 according to a preferred embodiment, comprising a gantry frame 302, a rotatable gantry structure 304 including beam members 306 and ring members 308 and 309, and a therapeutic radiation head 310 including an end collimator 312. The IGRT system 300 is similar to the IGRT system 200 of FIGS. 2A-2C except that the beam member 306 upon which the therapeutic radiation head 310 is mounted is approximately linear and oriented approximately horizontally. A lesser SAD is provided for therapeutic radiation head 310 at locations nearer the transverse isocentric plane 217 than for locations nearer the ends of the beam member 306.

Figure 4A:
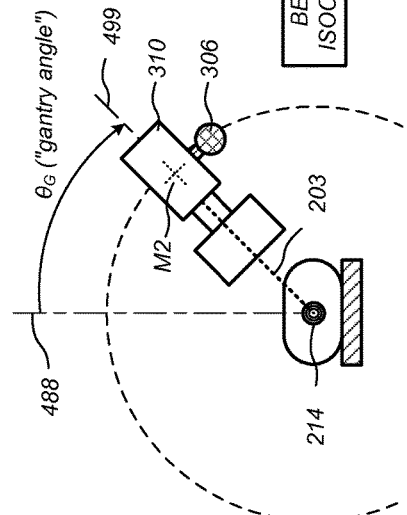
FIGS. 4A-4D illustrate radiation treatment head pivoting capability in an IGRT system according to a preferred embodiment.
Figure 4C:
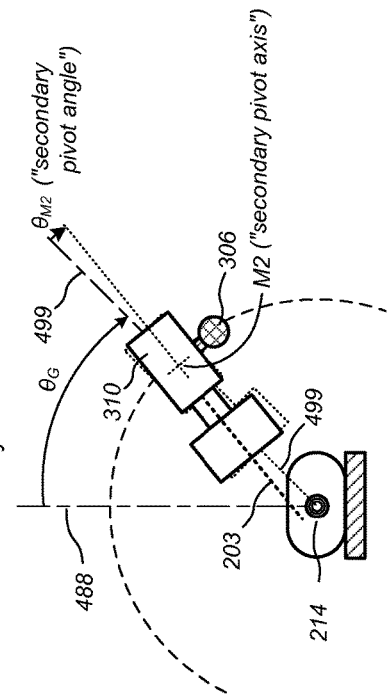
Figure 4B:
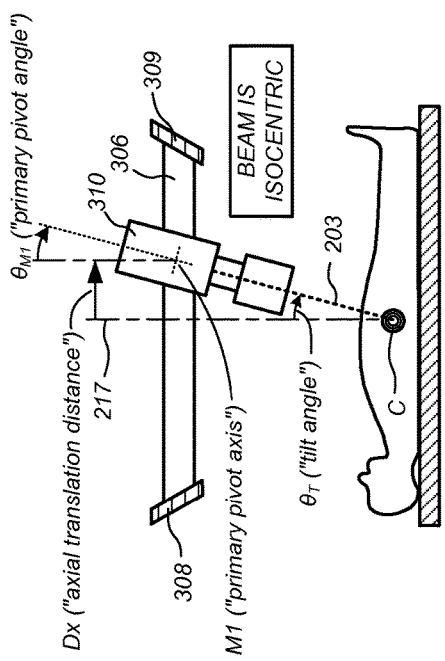

FIGS. 4A-4D are presented to provide definitions for the functional geometry of an IGRT system according to the preferred embodiments, and are presented by way of a nonlimiting example with respect to the IGRT system 300 of FIGS. 3A-3B. With reference to FIG. 4A, an axial translation distance Dx is defined as a translation distance of the therapeutic radiation head 310 along the beam member 306 relative to an arbitrary reference point therealong, which can be set at the transverse isocentric plane 217 as in FIG. 4A or at another fixed location along beam members 306. A tilt angle $\theta_T$ is defined as the arc between the therapeutic radiation beam 203 and the transverse isocentric plane 217 when the therapeutic radiation beam 203 is at isocenter. For any fixed position of the therapeutic radiation head 310 along the beam member 306, the tilt angle $\theta_T$ is fixed. A primary pivot angle $\theta_{M1}$, also termed an M1 pivot angle, is defined as the net amount the therapeutic radiation head 310 has been rotated around its M1 axis relative to an arbitrary starting orientation therearound, which can be set at parallel to the transverse isocentric plane 217 as in FIG. 4A or at some other fixed starting orientation. For the particular case of a straight beam member 306 that is approximately horizontal, as in FIG. 4A, the primary pivot angle $\theta_{M1}$ is equal to the tilt angle $\theta_T$ when the therapeutic radiation beam 203 is at isocenter. Illustrated in FIG. 4B is a scenario in which the primary pivot angle $\theta_{M1}$ has changed by a small amount $\Delta\theta_{M1}$ relative to the configuration of FIG. 4A, which has caused the therapeutic radiation beam 203 to become off-isocenter.

Figure 4D:
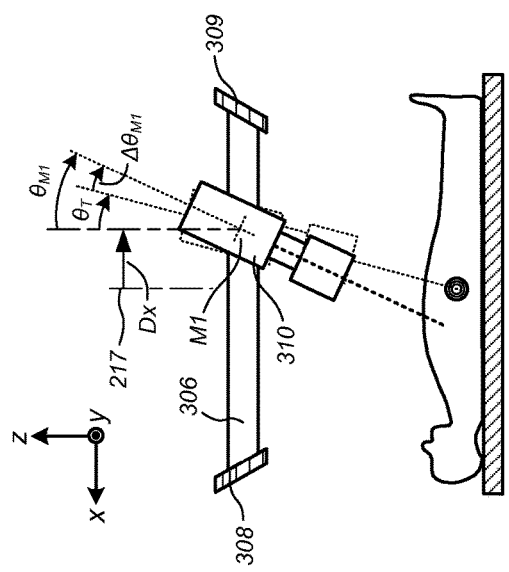

With reference to FIG. 4C, a gantry angle $\theta_G$ is defined as the net amount the rotatable gantry structure 304 has been rotated around the rotation axis 214 relative to an arbitrary starting orientation therearound, which is illustrated by a vertical line 488 in FIG. 4C. With reference to FIG. 4D, a secondary pivot angle $\theta_{M2}$, also termed an M2 pivot angle, is defined as the net amount the therapeutic radiation head 310 has been rotated around its M2 axis relative to an arbitrary starting orientation therearound, which can correspond to a starting case (see FIG. 4C) in which the therapeutic radiation beam 203 is at isocenter. Illustrated in FIG. 4D is a scenario in which the secondary pivot angle $\theta_{M2}$ has been moved to a value other than zero, which has caused the therapeutic radiation beam 203 to become off-isocenter. In one preferred embodiment, the M1 and M2 pivot angles are dynamically varied during treatment to compensate for target volume motions (caused by, e.g., breathing motions or patient movement) while the patient couch 222 remains stationary, thereby facilitating increased treatment effectiveness against patient movement while also allowing the patient to be more comfortable and at-ease as compared to configurations in which the patient couch 222 is moved. In another preferred embodiment, the M1 and M2 pivot angles are varied to deliver radiation beams non-isocentrically, which can for example allow the treatment of targets that are larger than the collimator field size without moving the patient couch 222.

FIGS. 5A-5B illustrate an IGRT system 500 according to a preferred embodiment that is similar to the preferred embodiment of FIGS. 3A-3B, but with the addition of in-treatment stereoscopic x-ray imaging sources ("kV sources") 552 and detectors ("kV detectors") 554. The kV sources 552 and kV detectors 554 are positioned in fixed, non-moving positions relative to the gantry frame 302 at locations designed to keep them out of contact with the therapeutic radiation head 310 during treatment. The kV sources 552 and kV detectors 554 are coplanar with the transverse isocentric plane 217. Shown in FIGS. 5A-5B are arrows labeled $S_{IMG}$ that are representative of the imaging radiation passing from each kV source 552 to its associated kV detector 554. For clarity of description herein, each kV source/detector pairing is referenced as a "kV imaging system." Although in the example of FIGS. 5A and 5B the kV imaging systems are coplanar with the transverse isocentric plane 217, in other preferred embodiments one or more of the kV imaging systems can be positioned out of the transverse isocentric plane 217. In one preferred embodiment, multiple kV imaging systems can be mounted to define one or more planes that are coincident with the rotation axis 214.

Figures 6A, 6B:
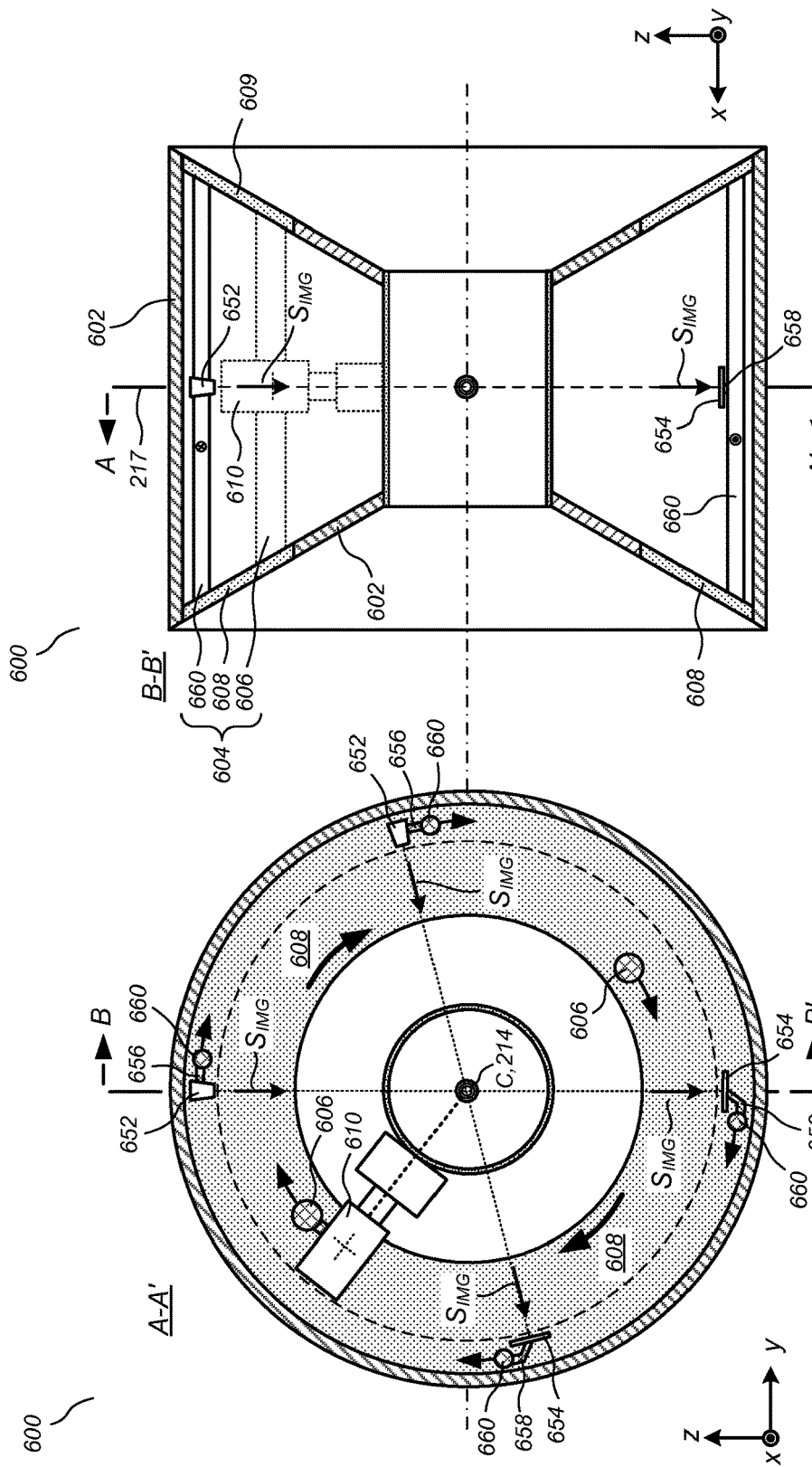
FIGS. 6A-6B illustrate axial and side cut-away views, respectively, of an IGRT system according to a preferred embodiment.
Figure 6C:
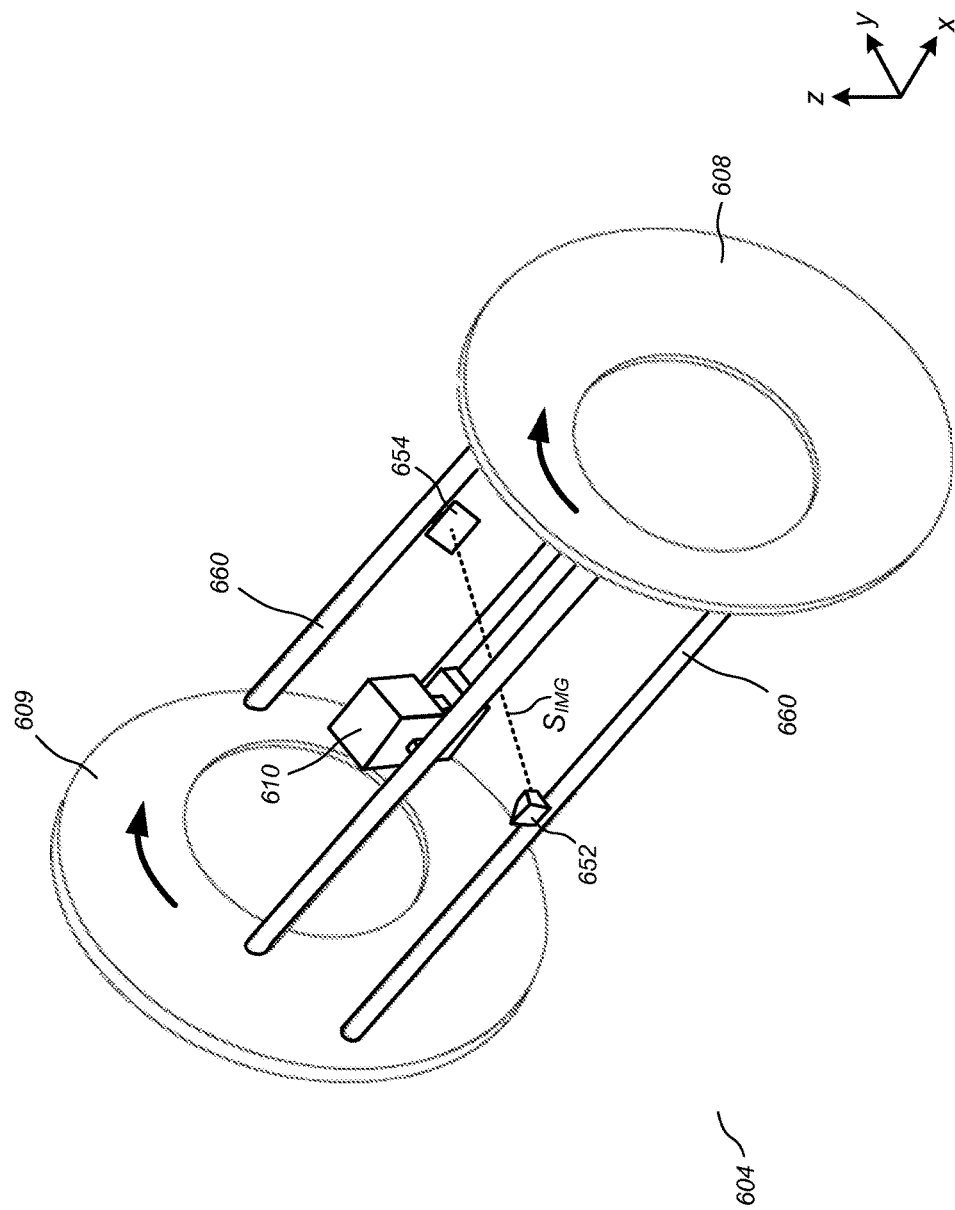
FIG. 6C illustrates a perspective view of a rotatable gantry structure of the IGRT system of FIGS. 6A-6B.

FIGS. 6A-6C illustrate an IGRT system 600 according to a preferred embodiment, comprising a gantry frame 602, a rotatable gantry structure 604 including beam members 606 and ring members 608 and 609, and a therapeutic radiation head 610. The IGRT system 600 is similar to the IGRT system 300 of FIGS. 3A-3B except that the rotatable gantry structure 604 is further provided with additional beam members 660 extending between ring members 608 and 609. The additional beam members 660 are each provided with one (or more) kV source(s) 652 and/or one (or more) kV detectors 654, and are configured such that each kV source 652 is paired with an associated kV detector 654 opposite the isocenter. Each kV source 652 is coupled to its respective beam member 606 by a respective coupling device 656, and each kV detector 654 is coupled to its respective beam member 606 by a respective coupling device 658, the coupling devices 656 and 658 being configured and adapted to achieve the functionalities (e.g., fixed, translational, and/or rotational) described further herein. For the preferred embodiment of FIGS. 6A-6C, there are four beam members 660 that establish two kV imaging systems. (FIG. 6C omits one of the kV imaging systems and its associated beam members for clarity of presentation.) In other preferred embodiments, there may only be a single kV imaging system provided, or more than two kV imaging systems provided. The beam members 660 are disposed at suitable angles relative to each other and to the therapeutic radiation head 610 to achieve the desired kV imaging functionality, which can include stereoscopic imaging or CT imaging (e.g., cone beam CT or CBCT imaging) when combined with rotation of the kV imaging system about the patient.

Figure 7:
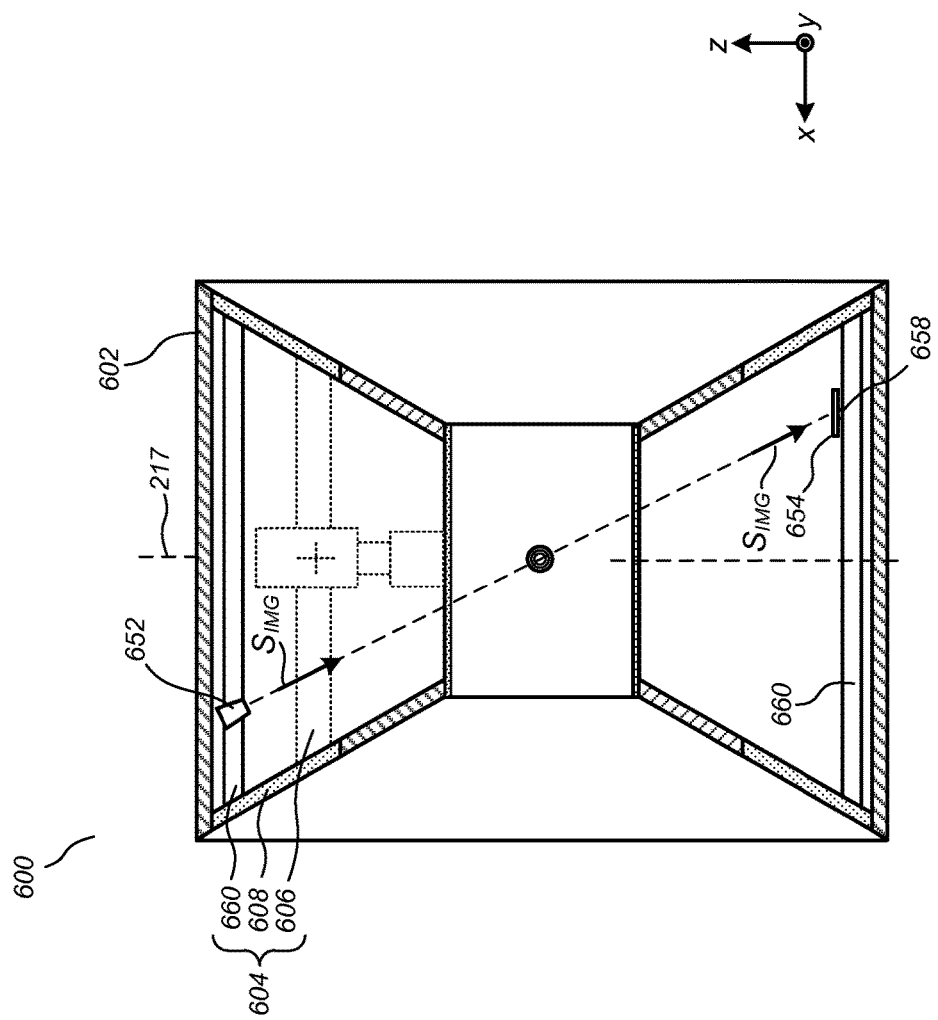
FIG. 7 illustrates an alternative embodiment of the IGRT system 600 of FIGS. 6A-6C.

FIG. 7 illustrates the IGRT system 600 of FIGS. 6A-6C as provided with an optional additional functionality in which the kV source(s) 652 and kV detector(s) 654 are axially translatable along their respective beam members. The kV source(s) 652 (and, optionally, the kV detectors 654) are also provided with pivoting or gimballing ability. As illustrated in FIG. 7, the kV imaging systems have the ability to depart from the transverse isocentric plane 217 in a variety of different ways. For the preferred embodiment of FIGS. 6A-6C and FIG. 7, the kV imaging systems rotate around the rotation axis 214 in unison with the therapeutic radiation head 610.

Figures 8A, 8B:
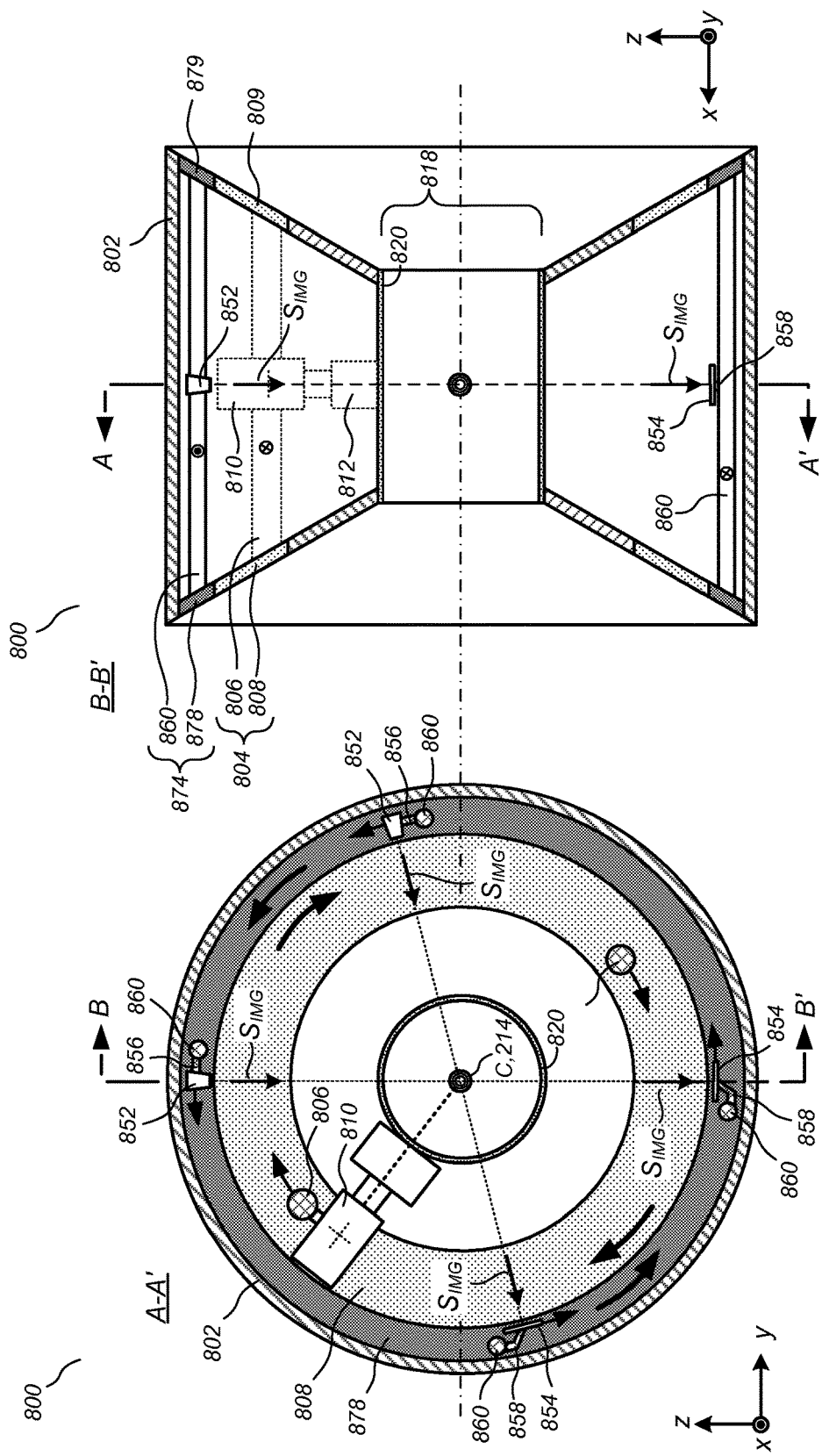
FIGS. 8A-8B illustrate axial and side cut-away views, respectively, of an IGRT system according to a preferred embodiment.
Figure 8C:
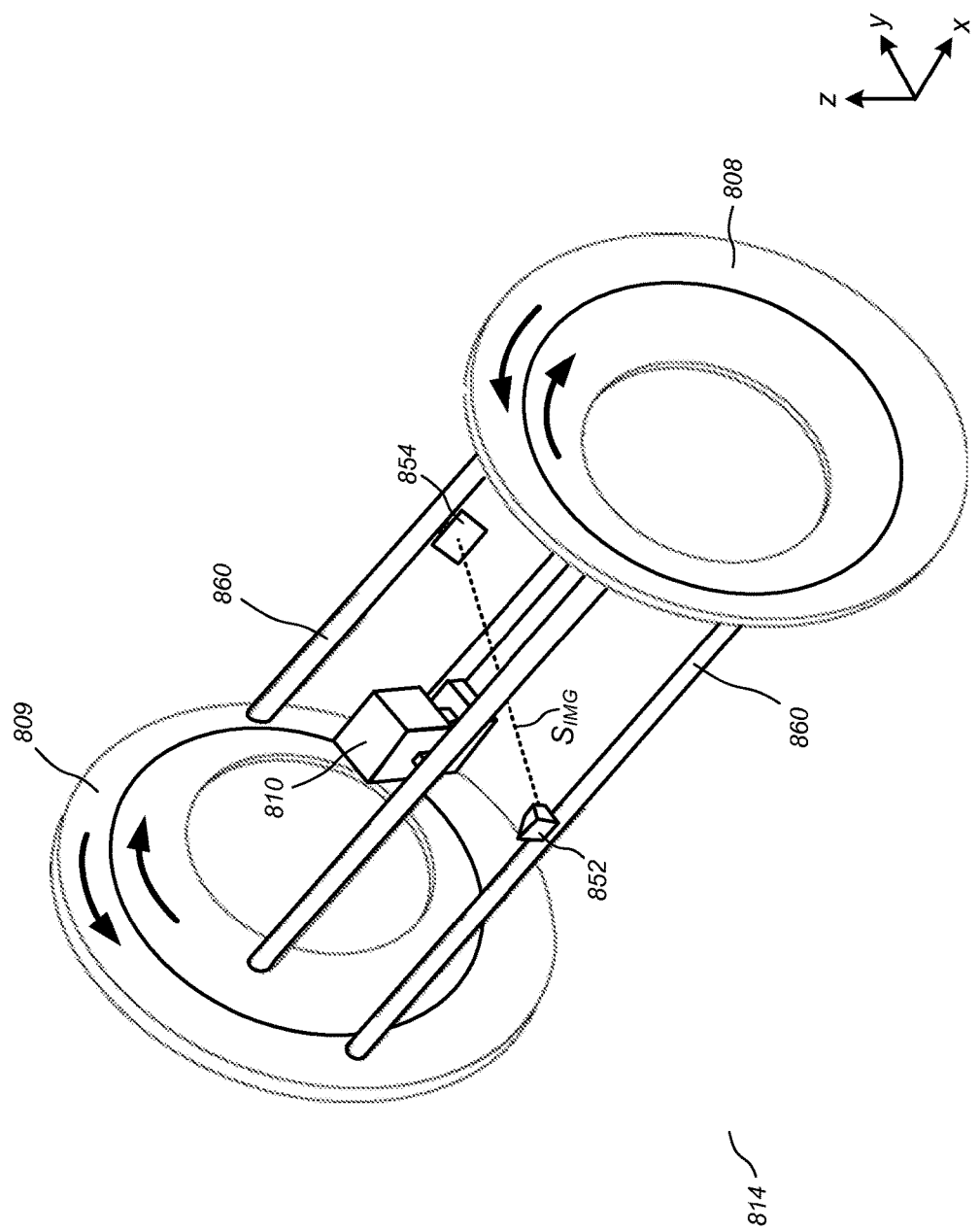
FIG. 8C illustrates a perspective view of plural rotatable gantry structures of the IGRT system of FIGS. 8A-8B.

FIGS. 8A-8C illustrate an IGRT system 800 according to a preferred embodiment in which the kV imaging system(s) rotate independently of the therapeutic radiation head around the rotation axis. IGRT system 800 comprises a gantry frame 802, a first rotatable gantry structure 804 including beam members 806 and ring members 808 and 809, and a therapeutic radiation head 810. IGRT system 800 further comprises a second rotatable gantry structure 874 including beam members 860 extending between a first ring member 878 and a second ring member 879, the second rotatable gantry structure 874 being configured and adapted to rotate concentrically with, and independently of, the first rotatable gantry structure 874 around the rotation axis 214. The IGRT system 800 comprises kV source(s) 852 each coupled to their respective beam member 806 by a respective coupling device 856, and kV detector(s) 854 each coupled to their respective beam member 806 by a respective coupling device 858, the coupling devices 856 and 858 being configured and adapted to achieve fixed, translational, and/or rotational functionalities between the kV source(s) 852/kV detector(s) 854 and their respective beam members 860. (FIG. 8C omits one of the kV imaging systems and its associated beam members for clarity of presentation.) Advantageously, because the kV imaging system(s) can rotate independently of the therapeutic radiation head around the rotation axis, a wide variety of setup and in-treatment imaging options are provided, for accommodating a rich variety of radiation therapy profiles and strategies. With regard to the orientation angles between respective kV imaging systems, 60 degrees or more is desirable for stereoscopic localization, while a full 90 degrees is optimal. For the preferred embodiment of FIGS. 5A-5B (static kV imaging system) and the preferred embodiment of FIGS. 8A-8C (fully decoupled from the therapeutic radiation head rotation), the choice of distances from the rotation axis 214 is somewhat limited, while for the preferred embodiment of FIGS. 6A-6C, in which the kV imaging systems rotate rigidly with the therapeutic radiation head rotation, that choice of distances is more flexible, for example, there is the ability to use a smaller kV detector and reduce the distance from the rotation axis 214.

FIGS. 9A-9C illustrate methods for non-coplanar rotational arc therapy using, by way of nonlimiting example, the IGRT system 800 of FIGS. 8A-8C, a simplified version of which is reproduced in FIG. 9A. In one preferred embodiment referenced herein as conical non-coplanar rotational arc therapy, the therapeutic radiation head 810 is axially translated along the beam member 806 in discrete steps, with a gantry rotation occurring at each step. There can be discrete firings of the therapeutic radiation beam at respective discrete gantry angles, or there can be continuous firings of the therapeutic radiation beam as the gantry angle is continuously changed, each of which are within the scope of the present teachings. FIG. 9B illustrates a cross-section of the resultant delivery profile for conical non-coplanar rotational arc therapy, with each discrete cone shape 1-5 corresponding to a different translational step of the therapeutic radiation head 810. In another preferred embodiment referenced herein as cono-helical non-coplanar rotational arc therapy, the therapeutic radiation head 810 is translated along the beam member 806 as the gantry is rotated. There can be discrete firings of the therapeutic radiation beam at respective discrete gantry angles (and correspondingly discrete translational advances of the therapeutic radiation head 810), or there can be continuous firings of the therapeutic radiation beam as the gantry angle is continuously changed (and correspondingly continuous translational advances of the therapeutic radiation head 810), each of which are within the scope of the present teachings. FIG. 9C illustrates a cross-section of the resultant delivery profile for conohelical non-coplanar rotational arc therapy, which spans the same conical three-dimensional volume as conical non-coplanar rotational arc therapy, but which does so in a continuous or helical manner.

Although certain examples in the discussion above and below are made with respect to the IGRT system 800 of FIGS. 8A-8C, which is particularly versatile, other of the preferred IGRT systems described hereinabove could also achieve various ones of the functionalities discussed herein as would be apparent to a person skilled in the art. Thus, it is to be appreciated that references in the discussion above and below to the IGRT system 800 of FIGS. 8A-8C are set forth by way of example and not my way of limitation.

As illustrated by the examples of FIGS. 9A-9C above, a rich variety of radiation therapy profiles and strategies can be accommodated using the IGRT system 800. Such possibilities include, but are not limited to: single or parallel opposed static beams with rectangular field shaping and 1D (wedge or virtual wedge using MLC) intensity modulation; static beams with rectangular field shaping and 1D modulation; coplanar rotational treatments ("arc therapy") with rectangular field shaping and 1D modulation; coplanar or non-coplanar beams with irregular field shaping and 1D modulation ("conformal radiation therapy" or CRT); coplanar or non-coplanar beams with irregular field shaping and 2D modulation ("intensity modulated radiation therapy" or IMRT); and tomotherapy (helical or sequential) with coplanar rotation using a narrow beam in combination with couch movement and 2D modulation. Such possibilities further include rotational arc therapy, also called intensity modulated arc therapy (IMAT), including one or more coplanar rotations, irregular field shaping, and 2D modulation, with gantry rotation speed, dose rate, MLC positions, and in some cases collimator angles being varied during rotation, and including multiple rotations that increase the achievable degree of intensity modulation in view of practical constraints on MLC motion during treatment.

One of the benefits of the IGRT system 800 is achieving rotational arc therapy with multiple non-coplanar rotations in order to maximize the number of beam positions, the solid angle covered by these positions, and the degree of intensity or fluence modulation of the therapeutic radiation beam in order to achieve the highest possible treatment plan quality. Another of the benefits of the IGRT system 800 is accurate delivery of treatment plans using image guidance for patient set up and intra-fraction motion tracking and correction. Another of the benefits of the IGRT system 800 is increased rigidity, which enables higher rotation speeds, higher delivery accuracy (less error in radiation beam position and orientation), and higher 3D reconstructed image quality (less error in imaging system geometry during rotation).

For one preferred embodiment, the therapeutic radiation head 810 comprises a compact lightweight LINAC, such as an X-band or C-band LINAC in a compact configuration without a bending magnet. This allows a compact system design in which all moving components are behind a fixed surface covering (see bore shield 820), thus eliminating the risk of collision with the patient and enabling higher rotation speeds (there is a U.S. regulatory standard that does not allow rotation speeds higher than one rotation per minute if there is a risk of collision with the patient). In other alternative embodiment, the compact accelerator can include a bending magnet.

By way of example and not by way of limitation, the central bore 818 could have a diameter of 85 cm. This will accommodate the vast majority of patients. The therapeutic radiation head 810 could be a LINAC having a distance from the radiation source target to the distal face of the end collimator 812 of 40 cm. In this case the SAD is approximately 82.5 cm (40 cm plus half of 85 cm) when the therapeutic radiation head 810 is in the transverse isocentric plane 217 (zero tilt angle). When the LINAC is tilted off axis by 30 degrees, the SAD is approximately 89.1 cm assuming negligible collimator size. The LINAC could have a length of approximately 214 cm. The outer diameter of the gantry frame 802 would then be approximately 3.1 m, which will fit within most existing treatment vaults. When the LINAC is tilted off axis by 30 degrees, the SAD will be larger than 89.1 cm with an actual collimator in order to keep the collimator outside the gantry bore. The SAD will increase with collimator size.

For one embodiment, external cables could be run to the therapeutic radiation head 810, the kV imaging systems, and the relevant actuators to provide electrical power and signals. This would require gantry rotations in alternating directions in order to wind and unwind the cables. More preferably, the rotatable gantry structure 804 and rotatable gantry structure 874 are configured with slip-ring technology, as known to the skilled artisan, for providing power and signals to these devices.

The therapeutic radiation head 810 could be a LINAC configured with different secondary collimation systems, including fixed cones, a variable aperture collimator such as the Iris Variable Aperture Collimator (Accuray Incorporated, Sunnyvale, Calif.), a binary (tomotherapy) collimator, or an MLC. The LINAC could optionally be configured with rectangular jaws.

In the discussion that follows, the therapeutic radiation head 810 is assumed to be a LINAC by way of example only and not by way of limitation, and the phrases "rotating the gantry" or "gantry rotation" refer to rotation of the rotatable gantry structure 804. Advantageously, there are many possible modes of operation for the IGRT system 800. The LINAC can rotate about the patient without tilting off axis. In this case it could treat at a discrete set of fixed gantry rotation angles (coplanar beams) with or without irregular field shaping and with or without modulation, thus enabling coplanar static beams, CRT, and IMRT. For each fixed gantry rotation angle, the LINAC can be tilted off axis at a tilt angle, thus enabling non-coplanar CRT and IMRT. Alternatively, the LINAC could be configured with a binary collimator or an MLC and deliver radiation while continuously rotating without tilting off axis. By combining the LINAC rotation with patient movement through the central bore 818, which can be accomplished for example by linear translation of the patient couch 222, sequential or helical tomotherapy is enabled. Alternatively, the LINAC could be configured with a MLC and deliver radiation while rotating the gantry without tilting off axis. The gantry rotation speed, dose rate, MLC shapes, and collimator angle could be varied during gantry rotation, thus also enabling conventional coplanar rotational arc therapy. By also tilting the LINAC off axis as the gantry angle is varied, it is possible to deliver rotational arc therapy with multiple non-coplanar rotations in order to maximize the number of beam positions, the solid angle covered by these positions, and the degree of intensity or fluence modulation in order to achieve the highest possible treatment plan quality. In one approach, the tilt angle is held constant while the gantry angle is varied. In another approach, the tilt angle is varied while the gantry angle is also varied (see FIGS. 9A-9C, conical non-coplanar rotational arc therapy and cono-helical rotational arc therapy). This approach could be combined with movement of the patient couch 222 during gantry rotation to provide what is termed herein conical non-coplanar tomotherapy or cono-helical non-coplanar tomotherapy. Because of the ability to achieve many orientations using gantry rotation (between 0 and 360 degrees) and moving the source out of plane by varying the tilt angle (within the maximum limits of the system, which could for example be −30 to +30 degrees, or −45 to +45 degrees), breast treatments with parallel opposed fields could be easily and quickly performed by setting the appropriate gantry rotation and tilt angles.

With one kV imaging system or less preferably with a portal imaging system, the system can acquire X-ray images during gantry rotation. The sequence of X-ray images can be used to reconstruct a cone beam CT (CBCT) image with many images acquired over at least 180 degrees of rotation. With fewer images acquired during a rotation of less than 180 degrees, the images can be used to reconstruct a tomosynthesis image. A CBCT image with a longer axial field of view can be reconstructed from a sequence of X-ray images acquired while moving the patient couch during gantry rotation. A CBCT image can be used for patient set up for example by registration of the CBCT to the planning CT image and aligning the target volume with isocenter in accordance with information obtained from the image registrations by adjusting the position of patient couch 222. The patient couch 222 could be used to correct for translation offsets and some or all rotation offsets between the CBCT image and the planning, pre-treatment CT image. Because of the ability to achieve any orientation defined by a gantry rotation angle and a tilt angle, all rotation offsets can be handled by adjusting the rotation and tilt angles appropriately. With two (or more) kV imaging systems, the system can acquire stereo X-ray images simultaneously or closely in time. The two (or more) X-ray images can be used for patient set up for example by registration of the X-ray images to digitally reconstructed radiographs (DRRs) generated from the planning CT image. With two kV imaging systems, it is possible to acquire X-ray images from both systems during gantry rotation. The images can be acquired simultaneously or interleaved to reduce scatter. If the imaging systems are mounted perpendicular to each other, it is possible to acquire all X-ray images required for CBCT image reconstruction with 90 degrees of gantry rotation rather than 180 degrees.

The ability to generate intra-treatment stereoscopic images or CBCT images allows for intra-fraction target motion tracking. Intra-fraction motion tracking and correction helps enable better treatment plans and the accurate delivery of those treatment plans. A system for correlating target motion with motion of an anatomical feature of the body (for example and without limitation external chest wall or a moving boney structure) can also be included in embodiments of the present invention. For example, a lung tumor will move periodically with respiration, and the tumor location can be correlated with (for example and without limitation) motion of the chest wall as the patient breaths (Accuray's Synchrony® System works in this manner). A camera can be fixed inside the bore shield 820 to monitor the motion of beacons placed on the external chest wall, which motion is correlated to the motion of the target due to respiration. Furthermore automated control of the M1 and M2 pivot angles during the fraction can be used to continuously aim the radiation beam at the desired location of a moving target. Other ways of moving the radiation beam to track with the moving target using the embodiments of the present invention will be appreciated by the skilled artisan.

With two or more kV imaging systems, the system can acquire stereo X-ray images simultaneously at any gantry rotation angle. With one kV imaging system, the system can acquire stereo X-ray images non-simultaneously at different gantry rotation angles (separated for example by 90 degrees). Advantageously, a compact design is provided in which all moving components are behind a fixed surface covering, thus eliminating the risk of collision with the patient and enabling higher rotation speeds than with conventional C-arm gantry systems. A higher gantry rotation speed allows the time between the sequential images to be reduced and for some applications this may provide sufficiently accurate tracking results.

Advantageously, also provided by the IGRT system 800 is a capability for sliding CBCT reconstruction. For one preferred embodiment, the rotatable gantry structure 874 can rotate synchronously with the rotatable gantry structure 804 (or, alternatively, the IGRT system of FIGS. 6A-6C can be employed). A CBCT can be reconstructed from a set of X-ray images acquired by the kV imaging system(s) during gantry rotation. One approach is to acquire X-ray images during gantry rotation, reconstruct the CBCT image, register it to the planning CT image, adjust the patient position as necessary, then begin treatment delivery. As rotation continues, additional X-ray images are acquired, and a continuously sliding window of the last N images (where N is variable, and can for example be the number of images corresponding to 180 degrees of rotation) is used to reconstruct a sequence of CBCT images, or alternatively a sufficient number of images are obtained to construct a new CBCT image. The newer images may replace older images at similar gantry angles, thereby updating the CBCT with newer images. Alternatively, when sufficient images become available a new CBCT can be generated to replace the previous CBCT. These CBCT images can be used for tracking and also for dose reconstruction. In other preferred embodiments, the rotatable gantry structure 874 can rotate independently of the rotatable gantry structure 804 for providing the CBCT images. Particularly where the decoupled rotatable gantry structure 874 is rotated at a relatively high rotation speed, which can advantageously be achieved in a stable manner by the IGRT system 800, a rich variety of new applications facilitated by real-time or quasi-real-time CBCT imaging are made possible including, but not limited to, cardiac applications.

Figure 10:
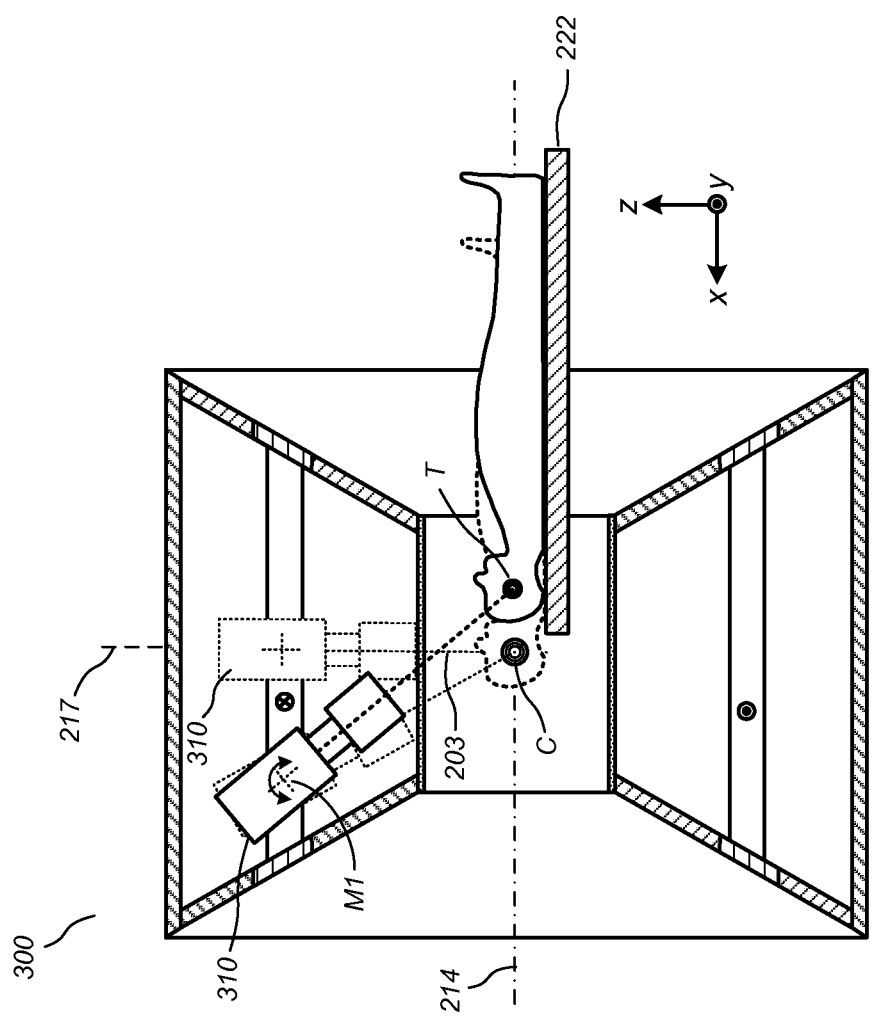
FIG. 10 illustrates non-isocentric radiation beam delivery using an IGRT system according to a preferred embodiment.

FIG. 10 illustrates non-isocentric beam delivery according to a preferred embodiment. It is an illustration of treatment with a treatment center T not at isocenter C. It is a method of increasing the tilt angle beyond what is otherwise possible for isocentric treatment. This can be especially useful for cranial applications but is also potentially useful for many extracranial applications. If the treatment center is moved along the rotation axis 214, then the therapeutic radiation beam can be made to go through the treatment center for all gantry rotation angles using an appropriate and fixed pivot about the M1 axis. Thus, advantageously, radiation treatment can be effectively provided for treatment centers not at isocenter. For a treatment center on the rotation axis 214, the radiation beam can be made to go through the treatment center with a fixed pivot about M1 axis.

Figure 11:
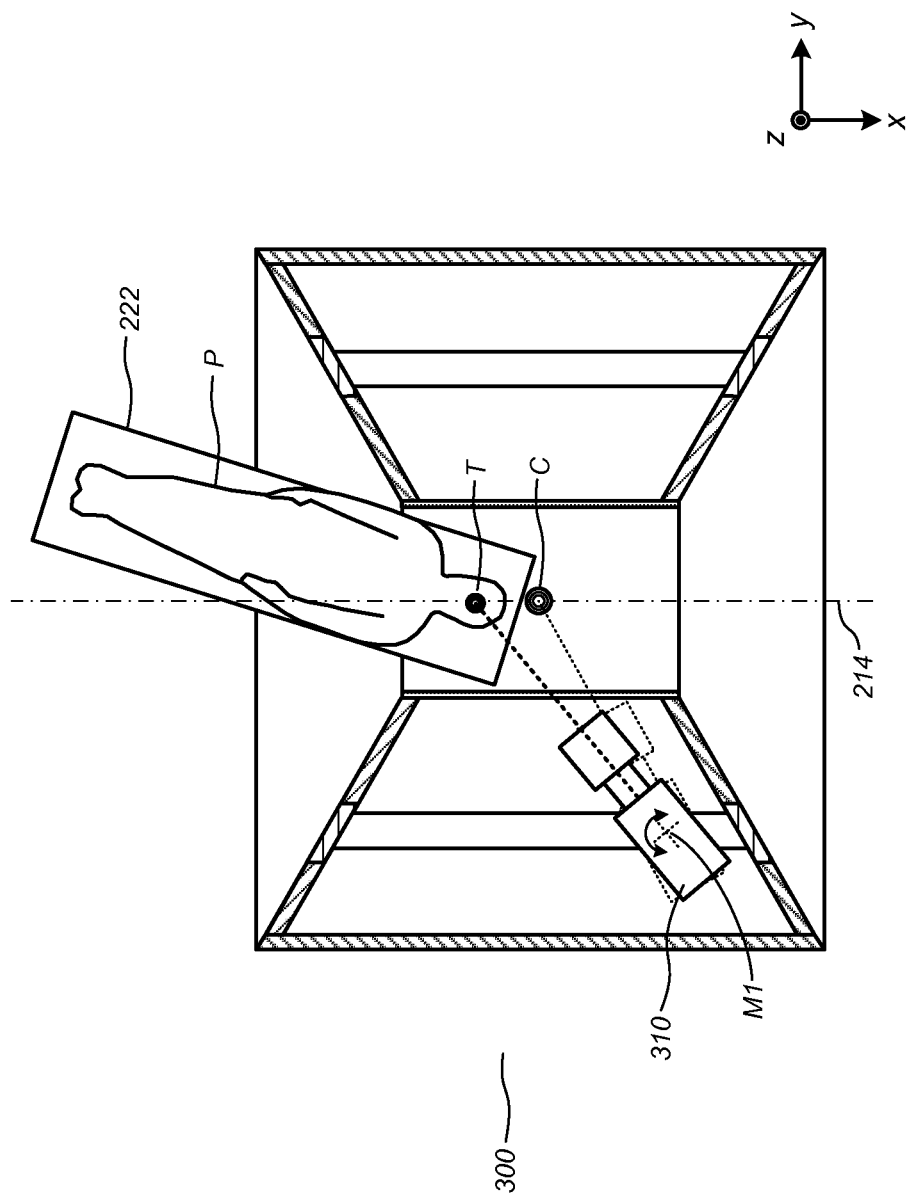
FIG. 11 illustrates non-isocentric radiation beam delivery including a couch kick using an IGRT system according to a preferred embodiment.

FIG. 11 illustrates using a so-called "couch kick" (moving the patient couch) in another mode of operation particularly useful for cranial treatments. This, in combination with the concepts above and in FIG. 10 for which a treatment center is not at isocenter, increases the available orientations for radiation beams going through the head.

According to another preferred embodiment (not shown) and described with respect to FIGS. 2A-2C above, there is provided a system in which the beam member 206 can be actuably moved outward and inward relative to the axis of rotation 214. For such preferred embodiment, the ends of the gantry frame 202 are preferably not tapered as in FIGS. 2A-2C, but rather are straight (planar) for easier mechanical implementation. The ring members 208 are also straight (planar) and made with a larger outer radius to accommodate different beam distances from the rotation axis 214. By such actuation the therapeutic radiation head 210 can be moved closer or further from the rotation axis 214, changing the SAD, even at a fixed translation distance along the beam member 206. Another advantage, in combination with the concepts for FIGS. 10 and 11, is an ability to keep the LINAC closer to the head (smaller SAD) for intracranial treatments and yet make the IGRT system versatile enough for other body parts.

FIG. 12 illustrates image guided radiation treatment using sliding-window tomosynthesis imaging according to a preferred embodiment. The method of FIG. 12 is preferably carried out using a gantry-style IGRT apparatus having a rotatable gantry structure and a treatment guidance imaging system, the treatment guidance imaging system being mounted to and rotatable with the rotatable gantry structure and having an x-ray cone beam projection imaging capability. At step 1202, a pre-acquired image data set is received, such as the 3D reference image 106 discussed supra with respect to FIG. 1, and which can alternatively be termed a planning image data set or reference image data set. The pre-acquired image data set, as that term is used herein, can refer not only to a particular 3D image volume that was acquired, but can alternatively refer to any expression or abstraction of that same information, such as DRRs or DRTs (digitally reconstructed tomographs) generated from that 3D image volume.

Figure 18:
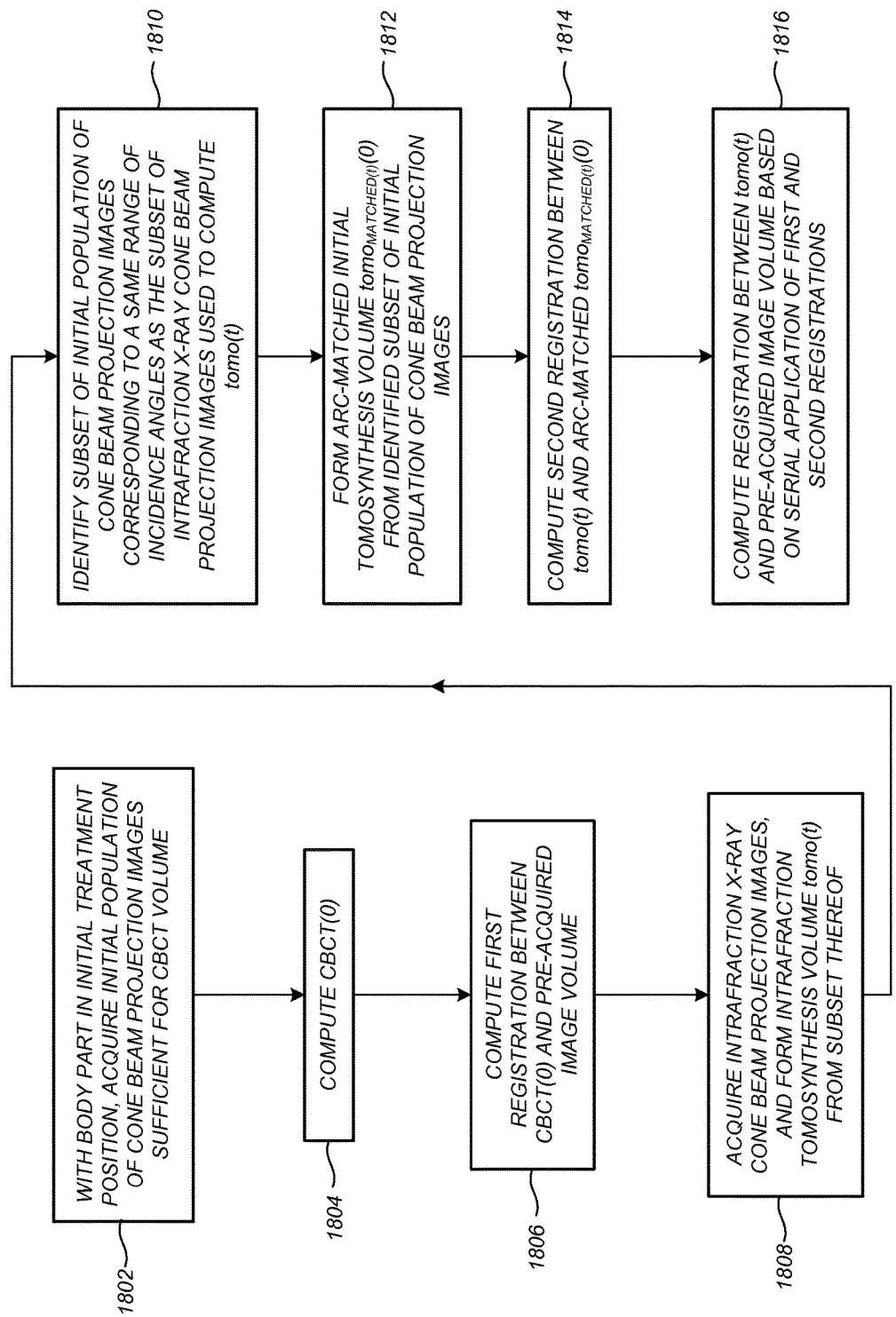

FIGS. 13A-16 illustrate selected examples of IGRT systems that can be used in carrying out the method of FIG. 12, as well as the methods of FIGS. 18-20 that are discussed further infra. It is to be appreciated that FIGS. 13A-16 are but a few examples of the many different IGRT system configurations that can be used in conjunction with the disclosed methods, and are disclosed by way of example only and not by way of limitation.

FIG. 13A illustrates, in an orthographic projection format (i.e., including front, top, and side views), an IGRT system 1300 that is similar in certain respects to the IGRT system of FIGS. 6A-6C, supra. The IGRT system 1300 comprises a barrel-style rotatable gantry structure G including beam members g1-g3 that rotate in unison around an axis of rotation through a range of gantry angles $\theta_G$. A radiation treatment head (therapeutic radiation source) "MV" is mounted to the beam member g2, an x-ray source array "XSA" is mounted to the beam member g1, and a digital detector array "D" is mounted to the beam member g3. For one preferred embodiment, the x-ray source array XSA comprises a computer-steerable electron beam and a spatial arrangement of metallic targets, each metallic target becoming an active x-ray focal spot when the electron beam is steered onto it, such as one or more such devices developed by Triple Ring Technologies, supra. However, other types of x-ray source arrays, such as cold-cathode source arrays, can alternatively be used. In other preferred embodiments, a conventional x-ray point source can be used instead of the source array XSA. More generally, for each of the illustrations of FIGS. 13A-16 there is an alternative preferred embodiment that is also within the scope of the present teachings in which one or more of the source arrays XSA is replaced by a conventional x-ray point source.

The x-ray source array XSA comprises a number of individual x-ray sources that are individually activatable, each individual x-ray source emitting x-ray radiation that is collimated, such as by an integral collimation device or an external collimation device (not shown) placed between that source and the target, into an x-ray cone beam that is projected through the body part and onto the digital detector array D. Any or all of the radiation treatment head MV, x-ray source array XSA, and digital detector array D can be pivotably and/or slidably mounted to the rotatable gantry structure G and correspondingly actuable under computerized control. Although digital detector arrays D are illustrated in the examples of FIGS. 13A-16 as being mounted on gantry beams opposite the x-ray source arrays, it is to be appreciated that the scope of the present teachings is not so limited, and that in other preferred embodiments one or more of the digital detector arrays D can be statically positioned (for example, immediately beneath the patient couch, or at selected floor or ceiling locations), or attached to the rotatable gantry structure in other suitable imaging configurations.

By virtue of a population of x-ray cone beam projection images acquired by operation of the x-ray source array XSA and digital detector array D, either or both of a tomosynthesis imaging capability and cone beam CT (CBCT) capability can be provided. Where a sufficient population of x-ray cone beam projection images is acquired over an imaging arc of at least 180 degrees plus a fan beam angle associated with the x-ray sources (termed herein a "minimum CBCT arc"), a three-dimensional CBCT reconstruction algorithm can be used to generate a CBCT volume, which is a "true" three-dimensional representation of the imaged volume. As known in the art, CBCT imaging can be differentiated from conventional CT imaging in that there is generally no collimation taking place at the detector, whereas conventional CT imaging involves a high degree of collimation at the detector, and therefore a CBCT volume will typically have an appreciably greater amount of noise due to scattering than a conventional CT volume. However, as also known in the art, CBCT imaging is generally faster and more easily implemented than conventional CT and represents a more realistic in-treatment imaging modality than conventional CT.

For cases in which the imaging arc is less than 180 degrees plus the fan beam angle (the minimum CBCT arc), a tomosynthesis reconstruction algorithm can be used to generate a tomosynthesis reconstructed volume. As known in the art, a tomosynthesis reconstructed image volume is less than "true" in that any particular slice therein will contain contributions from anatomical structures lying throughout the imaged volume, albeit in blurred form for structures lying outside that particular slice location. Although tomosynthesis reconstructed image volumes are generally of lesser quality and are more artifact-laden than CBCT images, tomosynthesis imaging provides an advantage that it is substantially faster to implement and, particularly for lesser imaging arcs, can be performed in near-real time or even real time, which is especially useful for in-treatment image guidance. According to one preferred embodiment, resolution loss associated with limited imaging arc, which is particularly heavy along an axis leading away from the x-ray source, is at least partially remedied by the use of stereoscopic tomosynthesis imaging.

FIG. 13B illustrates an IGRT system 1350 that is similar to the IGRT system 1300 of FIG. 13A, except with the addition of a stereoscopic tomosynthesis imaging capability. In particular, dual x-ray source arrays XSA1 and XSA2 and their associated digital detector arrays D1 and D2 are disposed in a stereoscopic imaging configuration relative to the treatment volume. For the example of FIG. 13B, the x-ray source arrays XSA1 and XSA2 are mounted on the same gantry beam g2, therefore being at a common rotational offset with respect to the axis of rotation of the rotatable gantry structure, and are positioned at different longitudinal positions therealong to define the stereoscopic imaging angle. For one preferred embodiment the stereoscopic imaging angle (i.e., the separation in incidence angle between the two "channels" of the stereoscopic configuration) is about 90 degrees, in other preferred embodiments is between 75 and 105 degrees, in still other preferred embodiments is between 45 and 135 degrees, and in still other preferred embodiments is between 25 and 155 degrees. For one preferred embodiment, respective tomosynthesis reconstructed image volumes based on the image data from the two stereo "channels" can be combined into a single tomosynthesis reconstructed volume, which is then processed according to the method of FIG. 12. Alternatively, the respective tomosynthesis reconstructed image volumes can be processed separately according to one or more of the steps of FIG. 12 and the results subsequently combined.

Figure 14:
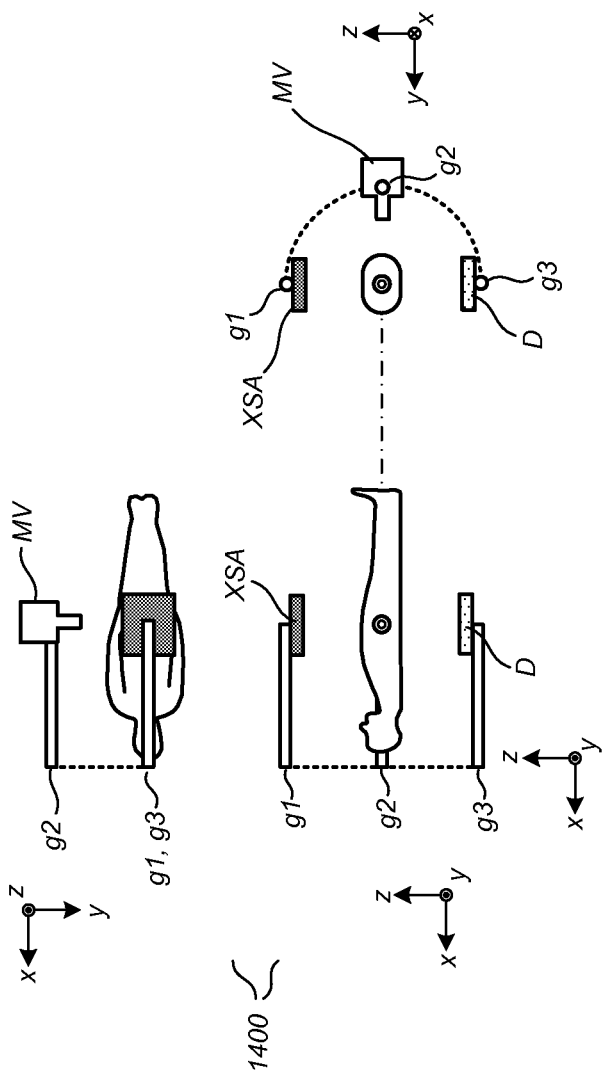
FIGS. 14-15 each illustrate front, top, and axial views of an IGRT system having one or more x-ray source arrays according to a preferred embodiment.

FIG. 14 illustrates an IGRT system 1400 that is similar to the IGRT system 1300 of FIG. 13A, except that a cantilever-style rotatable gantry structure is used rather than a barrel-style rotatable gantry structure. In other preferred embodiments, a ring-style rotatable gantry structure (not shown) can be used in conjunction with the methods of FIG. 12 and FIGS. 18-20. A variety of other rotating-gantry structures having at least one x-ray cone beam source mounted thereon are also within the scope of the present teachings.

Figure 15:
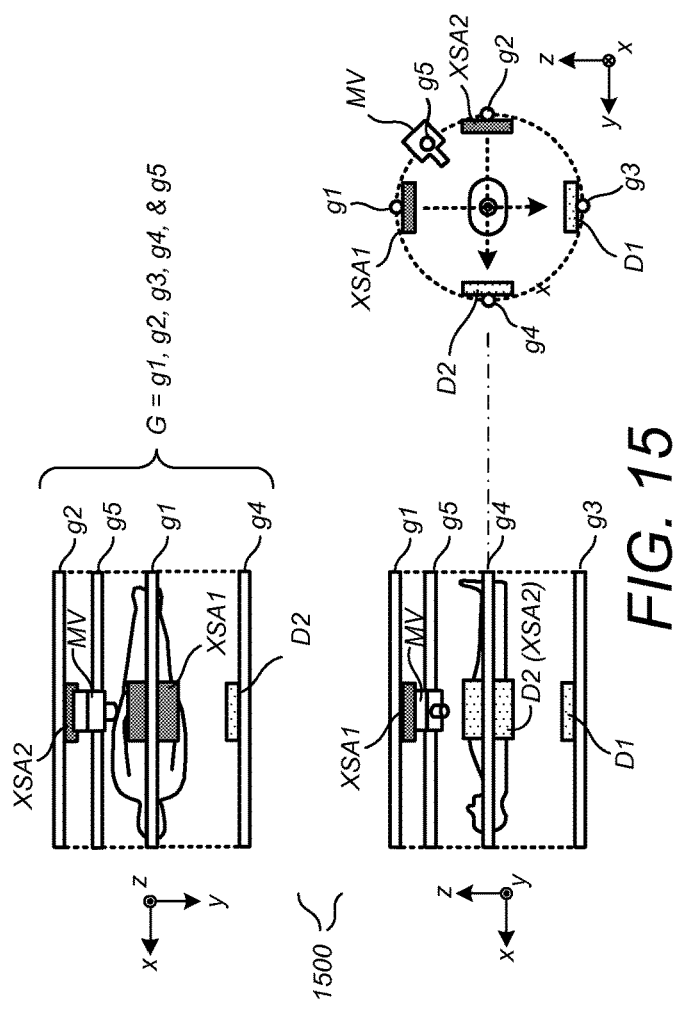

FIG. 15 illustrates yet another non-limiting example of an IGRT delivery architecture that can be used in conjunction with the described methods. FIG. 15 illustrates an IGRT system 1500 including a barrel-style gantry G having beam members g1-g5, a radiation treatment head MV, and dual source-detector pairs XSA1-D1 and XSA2-D2 configured in a stereoscopic imaging configuration. However, unlike the stereoscopic configuration of FIG. 13B, the source-detector pairs are mounted at a common longitudinal position along the rotatable gantry structure and positioned at different rotational offsets with respect to the axis of rotation to define the stereoscopic imaging configuration. A variety of different combinations of the longitudinal-offset configuration of FIG. 13B and the rotational-offset configuration of FIG. 15 to define the stereoscopic imaging configuration are also within the scope of the present teachings.

Figure 16:
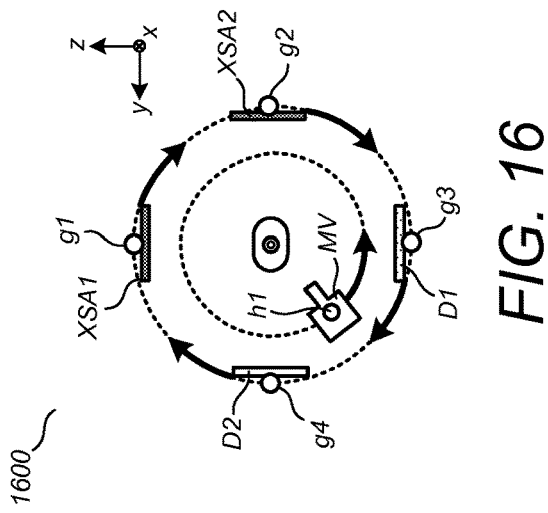
FIG. 16 illustrate an axial view of an IGRT system having one or more x-ray source arrays according to a preferred embodiment.

FIG. 16 illustrates yet another non-limiting example of an IGRT delivery architecture that can be used in conjunction with the described methods. FIG. 16 illustrates an IGRT system 1600 (side view only) that is similar to the IGRT system 1500 of FIG. 15, except that the stereoscopic tomosynthesis imaging hardware is mounted on a first rotatable gantry structure (having beam members g1-g5) and the radiation treatment head MV is mounted on a second rotatable gantry structure (having beam member h1). The second rotatable gantry structure rotates concentrically with, and independently of, the first rotatable gantry structure.

By way of example and not by way of limitation, the method of FIG. 12 is discussed further hereinbelow with respect to the exemplary IGRT system 1300 of FIG. 13A. At step 1204, during a patient setup interval, the patient is positioned into an initial treatment position relative to the IGRT system under the guidance of the treatment guidance imaging system. Without limitation, the source-detector pair XSA-D of the treatment guidance imaging system can be used to guide the patient setup process (using, for example, tomosynthesis, CBCT, or stereo x-ray imaging guidance) or, alternatively, a separate component of the treatment guidance imaging system, such as a separate on-board CBCT, ultrasound, tomosynthesis, or stereo x-ray imaging system, can be used to guide the patient setup process. At step 1206, after the beginning of radiation treatment delivery, the x-ray cone beam imaging source (e.g., x-ray source array XSA) and the imaging detector (e.g., the digital detector array D) are operated to acquire a first population of x-ray cone beam projection images of the body part for a respective first population of gantry angles and acquisition times. At step 1208, the first population of x-ray cone beam projection images is processed to compute therefrom a time sequence of sliding-window tomosynthesis reconstructed image volumes. The time sequence of sliding-window tomosynthesis reconstructed image volumes is characterized in that each subsequent member of the sequence is computed using at least one same x-ray cone beam projection image that was used in computing at least one previous member of the time sequence.

Figure 17:
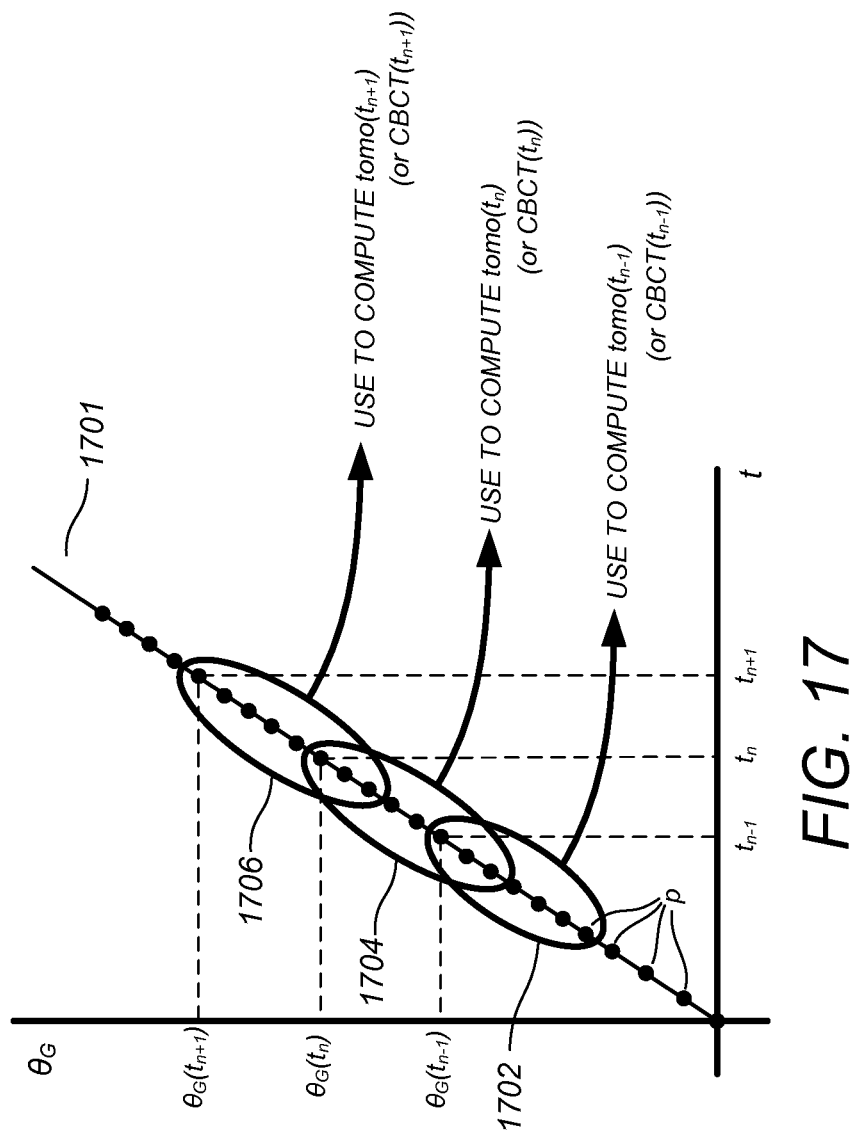
FIG. 17 illustrates a conceptual diagram of an example of sliding-window tomosynthesis imaging or sliding-window CBCT imaging according to one or more preferred embodiments.

FIG. 17 illustrates a conceptual plot 1701 of gantry angle $\theta_G$ versus time "t" during a treatment fraction. Although for clarity of disclosure the gantry angle trajectory is shown as a straight line in FIG. 17, which is indicative of a scenario in which the rotatable gantry structure rotates in the same direction at a constant rate, the described methods are applicable for a wide variety of different gantry angle trajectory scenarios in which the rotatable gantry structure can accelerate, decelerate, stop, reverse direction, and so forth, as would be apparent to a person skilled in the art in view of the present disclosure. Shown conceptually in FIG. 17 by points small circles "p" are x-ray cone beam projection images acquired during the treatment fraction. Each small circle "p" can represent a single x-ray cone beam projection image as may be acquired by a point source or a single member of an x-ray source array, or can alternatively represent many different x-ray cone beam projection images acquired at very closely spaced points in time. As illustrated in FIG. 17, respective overlapping subsets of x-ray cone beam projection images 1702, 1704, and 1706 (a "sliding window") are used to compute respective members tomo $(t_{n-1})$, tomo$(t_n)$, and tomo$(t_{n+1})$ of a time sequence of tomosynthesis reconstructed images. For one preferred embodiment, at least 50% of the x-ray cone beam projection images used to compute one member of the sequence of tomosynthesis reconstructed images are also used (more specifically, "re-used") to compute the next member of the sequence.

With reference again to FIG. 12, at step 1210 treatment radiation is delivered to the body part based at least in part on a comparison between each of the time sequence of sliding-window tomosynthesis reconstructed image volumes and the pre-acquired image data set. The use of sliding-window tomosynthesis reconstructed image volumes (and sliding-window CBCT volumes, see FIG. 19 infra) has been found advantageous in that an at least partially morphable or morphing characteristic or quality is imparted thereto that facilitates improved object identification and object tracking over time. The use of sliding-window tomosynthesis reconstructed image volumes (and sliding-window CBCT volumes) has also been found advantageous in that a beneficial balance is provided among the competing requirements of angular sufficiency of the data set, timewise newness of the data set, and anatomical similarity of adjacent members of the time sequence of reconstructed volumes. Another advantage is that, upon computation of one tomosynthesis reconstructed image volume, selected linear mathematical combinations among the re-used x-ray cone beam projection images (when there are a plurality of such re-used images) that were performed for the one tomosynthesis reconstructed image volume do not require recomputation for the next tomosynthesis reconstructed image volume in the sequence, thereby making the overall computational process more efficient.

FIG. 18 illustrates a method for advantageous multipurpose use of a population of x-ray cone beam projection images that can be optionally integrated into the method of FIG. 12, supra, wherein a common population of x-ray cone beam projection images is used in creating both an initial CBCT volume and selected initial tomosynthesis volumes for facilitating treatment guidance in an image guided radiation treatment system. At step 1802, with the body part in an initial treatment position (or alternatively at some other starting point in time during setup, upon setup, or near a beginning of the treatment delivery, termed herein an initial time), an initial population of x-ray cone beam projection images sufficient for creating a CBCT volume (i.e., extending over the minimum CBCT arc) is acquired. For preferred embodiments in which an x-ray source array is used, the CBCT volume will be what is termed herein an x-ray source array CBCT (XSA-CBCT) volume. At step 1804, an initial CBCT volume CBCT(0) is computed from the initial population x-ray cone beam projection images, and at step 1806 a first registration is computed between CBCT(0) and the pre-acquired image volume. At step 1808 (which corresponds generally to steps 1206-1208 of FIG. 12, supra) intrafraction x-ray cone beam projection images are acquired and processed to form a tomosynthesis volume tomo(t).

As with any tomosynthesis imaging process, there will be a certain tomosynthesis imaging arc (i.e., a set of angles of incident x-ray radiation upon the subject volume) associated with the particular subset of intrafraction x-ray cone beam projection images that were used to compute tomo(t) at step 1808. By way of explanation, let this tomosynthesis imaging arc be represented by the range $(\theta_{MIN}(t), \theta_{MAX}(t))$. For a scenario in which a single x-ray point source is used, the range $(\theta_{MIN}(t), \theta_{MAX}(t))$ will be defined according to the range of gantry angles traversed when acquiring the subset of x-ray cone beam projection images. For a scenario in which an x-ray source array is used and the gantry is not rotating during the particular acquisition interval in question, the range $(\theta_{MIN}(t), \theta_{MAX}(t))$ will be defined according to the imaging angles subtended by the different x-ray point sources as determined by their respective positions on the surface of the source array. For a scenario in which an x-ray source array is used and the gantry is indeed rotating during the particular acquisition interval in question, the range $(\theta_{MIN}(t), \theta_{MAX}(t))$ will be defined according to a combination of the gantry angle traversed and the range of imaging angles subtended across the surface of the array. According to a preferred embodiment, at step 1810, for any particular intrafraction tomosynthesis volume tomo(t), there is identified a subset of the initial population of x-ray cone beam projection images used to construct CBCT(0) that correspond in tomosynthesis imaging arc to the tomosynthesis imaging arc for tomo(t), i.e., that correspond to the incidence range $(\theta_{MIN}(t), \theta_{MAX}(t))$.

At step 1812, the subset of the initial population of x-ray cone beam projection images identified at step 1810 is then processed to form a separate tomosynthesis volume, which is referenced herein as an arc-matched tomosynthesis volume $tomo_{MATCHED(t)}(0)$. Advantageously, there will be an intrinsic, inherent registration between $tomo_{MATCHED(t)}(0)$ and CBCT(0) because they are computed using the same set of x-ray cone beam projection images. Therefore, the first registration between CBCT(0) and the pre-acquired image volume (e.g., planning CT) that was computed at step 1806 can be re-used to serve as the registration between $tomo_{MATCHED(t)}(0)$ and the pre-acquired image volume. At step 1814, a second registration between the intrafraction tomosynthesis volume tomo(t) and the arc-matched tomosynthesis volume $tomo_{MATCHED(t)}(0)$ is computed. Finally, at step 1816, a registration between tomo(t) and the pre-acquired image volume is computed based on (i) the first registration between CBCT(0) and the pre-acquired image volume, (ii) the inherent registration between $tomo_{MATCHED(t)}(0)$ and CBCT(0), and (iii) the second registration between tomo(t) and $tomo_{MATCHED(t)}(0)$. Treatment radiation is then delivered to the body part based at least in part on the results of the registration performed at step 1816.

Advantageously, the method of FIG. 18 provides the speed advantages associated with tomosynthesis-based image guidance during the intrafraction time frame, while also providing the precision advantages associated with the use of a full CBCT volume when performing the registration to the pre-acquired image volume (e.g., planning CT image). The latter aspect is particularly advantageous since registration between image volumes acquired using different imaging systems having different frames of reference—a process that could be called a "bridging" registration—can be a particularly difficult and error-prone process, and therefore it is advantageous to base the "bridging" registration on a higher quality CBCT image volume rather than a lower quality tomosynthesis volume. At the same time, the method of FIG. 18 only requires that the "bridging" registration be performed one time, upon acquisition of CBCT(0), and preferably prior to the onset of radiation delivery when time constraints are not critical. These same high-quality registration results can then be re-used during the radiation delivery period, when time constraints are more crucial to effective intrafraction target tracking. Advantageously, during the radiation delivery period when the time constraints are indeed more crucial, there are only "non-bridging" registrations required between tomo(t) and $tomo_{MATCHED(t)}(0)$, which can be quickly and reliably performed since those volumes were acquired using the same set of imaging hardware having a common frame of reference.

Image-guided radiation treatment according to the method of FIG. 12, which can optionally include the method of FIG. 18, will usually involve repetition of steps 1206-1210 throughout the treatment fraction, including the computation of a latest (i.e., most recent) member of the time sequence of sliding-window tomosynthesis reconstructed image volumes, comparing that latest member with the pre-acquired image data set, and delivering treatment radiation to the body part based on the results of that comparison. As used herein, the term latest gantry angle refers to the gantry angle associated with the most recent x-ray cone beam projection image used to form the latest member of the sequence of sliding-window tomosynthesis volumes. For one preferred embodiment, computation of the latest member of the sequence comprises receiving a first parameter indicative of a desired tomosynthesis reconstruction coverage arc, identifying from the acquired population of x-ray cone beam projection images a first subset thereof having corresponding gantry angles that are within the desired tomosynthesis reconstruction coverage arc of the latest gantry angle, and computing the latest member of the sequence of sliding-window tomosynthesis volumes based on that first subset. The tomosynthesis coverage arc will usually be about 6 degrees at a minimum and 180 degrees at a maximum, although the scope of the preferred embodiments is not so limited. As used herein, latest acquisition time refers to the time of acquisition of the most recent x-ray cone beam projection image used to form the latest member of the sequence of sliding-window tomosynthesis volumes. For one preferred embodiment, computation of the latest member of the sequence comprises receiving a second parameter indicative of a desired data aging threshold, identifying from the first subset of x-ray cone beam projection images a second subset thereof having corresponding acquisition times that are within the desired data aging threshold of the latest acquisition time, and computing the latest member using only that second subset of x-ray cone beam projection images.

The method can further comprise evaluating the percentage of x-ray cone beam projection images that are being re-used between the latest member of the time sequence of sliding-window tomosynthesis image volumes and the immediately preceding member of the sequence, this percentage being termed herein a window overlap ratio. The method can further comprise receiving a third parameter indicative of a desired window overlap ratio, and then adjusting one or more parameters of the IGRT system such that the actual window overlap ratio becomes closer to the desired window overlap ratio for future members of the time sequence. The one or more parameters can include, for example, the tomosynthesis reconstruction coverage arc(s), the data aging threshold, an acquisition rate of the x-ray cone beam projection images, and the time separation between future adjacent members of the time sequence.

One or more aspects of the method of FIG. 12, as well as one or more aspects of the methods of FIG. 18 and FIGS. 19-20 infra, can be carried out according to one or more of the methods described in one or more of the commonly assigned applications incorporated by reference above. For one preferred embodiment, comparing the latest member of the time sequence of sliding-window tomosynthesis reconstructed image volumes with the pre-acquired image data set comprises computing a digitally reconstructed tomosynthesis (DRT) image data set from the pre-acquired 3D image volume, processing the DRT image data set to compute a DRT image volume, and computing a registration between the latest member and the DRT image volume. Where the latest member of the intrafraction time sequence of tomosynthesis reconstructed image volumes is computed from a first subset of the population of x-ray cone beam projection images, the DRT image data set is computed from the pre-acquired 3D image volume using a virtual projection process, wherein each virtual projection is preferably based on the imaging geometry associated with a respective corresponding one of the first subset of the x-ray cone beam projection images.

For one preferred embodiment in which the treatment guidance imaging system uses tomosynthesis imaging for both setup and in-treatment imaging, an initial population of x-ray cone beam projection images is acquired, and a first registration between the initial tomosynthesis volume and the DRT image volume is carried out. The initial population of x-ray cone beam projection images is preferably acquired with the body part in an initial treatment position, or alternatively at some other starting point in time during setup, upon setup, or near a beginning of the treatment delivery, termed herein an initial time. Computation of the registration between the latest member of the time sequence of sliding-window tomosynthesis reconstructed image volumes and the DRT image volume is based upon (i) the first registration between the initial tomosynthesis image data set and the DRT image volume, and (ii) a second registration between the latest member and the initial tomosynthesis volume. For another preferred embodiment, comparison of the latest member of the time sequence of sliding-window tomosynthesis reconstructed image volumes with the pre-acquired image data set comprises a direct 3D-3D registration between the tomosynthesis reconstructed image volume and the complete 3D pre-acquired image volume.

FIG. 19 illustrates image guided radiation treatment using sliding-window CBCT imaging according to a preferred embodiment. The method of FIG. 19 is analogous in many respects to the method of FIG. 12, except that the imaging arc over which the population of x-ray cone beam projection images is acquired is at least 180 degrees plus the fan beam angle of the x-ray cone beam source, i.e., the minimum CBCT arc. Any of the systems of FIGS. 13A-16 can be used in conjunction with the method of FIG. 19, and the conceptual diagram of FIG. 17 is likewise applicable provided that a minimum CBCT arc is traversed in acquiring the subject subset of x-ray cone beam projection images. Stereo CBCT imaging can be likewise incorporated, with the configuration of FIG. 13B being particularly advantageous.

By way of example and not by way of limitation, the method of FIG. 19 is discussed further hereinbelow with respect to the exemplary IGRT system 1300 of FIG. 13A. At step 1902, a pre-acquired image data set is received. At step 1904, during a patient setup interval, the patient is positioned into an initial treatment position relative to the IGRT system. At step 1906, a first population of x-ray cone beam projection images of the body part for a respective first population of gantry angles and acquisition times is acquired, the first population of gantry angles extending at least over a minimum CBCT arc. At step 1908, the first population of x-ray cone beam projection images is processed to compute therefrom a time sequence of sliding-window CBCT reconstructed image volumes characterized in that each subsequent member of the time sequence is computed using at least one same x-ray cone beam projection image that was used in computing at least one previous member of the time sequence. At step 1910 treatment radiation is delivered to the body part based at least in part on a comparison between each of the time sequence of sliding-window CBCT volumes and the pre-acquired image data set.

Image-guided radiation treatment according to the method of FIG. 19, will usually involve repetition of steps 1906-1910 throughout the treatment fraction, including the computation of a latest (i.e., most recent) member of the time sequence of sliding-window CBCT volumes, comparing that latest member with the pre-acquired image data set, and delivering treatment radiation to the body part based on the results of that comparison. As used herein, the term latest gantry angle refers to the gantry angle associated with the most recent x-ray cone beam projection image used to form the latest member of the sequence of sliding-window CBCT volumes. For one preferred embodiment, computation of the latest member of the sequence comprises identifying from the acquired population of x-ray cone beam projection images a subset thereof having corresponding gantry angles that are between the minimum CBCT arc and 360 degrees away from the latest gantry angle, and computing the latest member based on that first subset.

For another preferred embodiment, computation of the latest member of the sequence of CBCT volumes comprises receiving a first parameter indicative of a desired CBCT coverage arc, which must of course be greater than or equal to the minimum CBCT arc, identifying from the acquired population of x-ray cone beam projection images a first subset thereof having corresponding gantry angles that are within the desired CBCT coverage arc of the latest gantry angle, and computing the latest member based on that first subset. The CBCT coverage arc will usually be between the minimum CBCT arc and 360 degrees. As used herein, latest acquisition time refers to the time of acquisition of the most recent x-ray cone beam projection image used to form the latest member of the sequence of sliding-window CBCT volumes. For one preferred embodiment, computation of the latest member of the sequence comprises receiving a second parameter indicative of a desired data aging threshold, identifying from the first subset of x-ray cone beam projection images a second subset thereof having corresponding acquisition times that are within the desired data aging threshold of the latest acquisition time, and computing the latest member using only that second subset of x-ray cone beam projection images.

As with the tomosynthesis-based method supra, the method of FIG. 19 can further comprise evaluating the percentage of x-ray ray cone beam projection images that are being re-used between the latest member of the time sequence of sliding-window CBCT volumes and the immediately preceding member of the sequence (window overlap ratio), and then adjusting one or more parameters of the IGRT system such that the actual window overlap ratio becomes closer to the desired window overlap ratio for future members of the time sequence. The one or more parameters can include, for example, the CBCT coverage arc(s), the data aging threshold, an acquisition rate of the x-ray cone beam projection images, and the time separation between future adjacent members of the time sequence.

For one preferred embodiment, comparing the latest member of the time sequence of sliding-window CBCT image volumes, which is referenced herein as CBCT(t), with the pre-acquired image data set comprises computing a direct 3D-3D registration between CBCT(t) and the pre-acquired 3D image volume. However, as with the tomosynthesis-based method supra, the method of FIG. 19 can alternatively leverage the advantages of a preferred registration scheme in which a "bridging" registration between image volumes acquired with different acquisition systems having different frames of reference only needs to be computed once per treatment fraction, and in which only "non-bridging" registrations need to be performed during the treatment fraction after the beginning of radiation delivery. Thus, for one preferred embodiment in which the treatment guidance imaging system uses CBCT imaging for both setup and in-treatment imaging, an initial population of x-ray cone beam projection images is acquired, an initial CBCT volume CBCT(0) is formed, and a first registration between CBCT (0) and the pre-acquired image volume is carried out. Subsequently, comparison of CBCT(t) against the pre-acquired image data set can be carried out by computing a second registration between CBCT(t) and CBCT(0), and then registering CBCT(t) to the pre-acquired image data set based on (i) the first registration between CBCT(0) and the pre-acquired 3D image volume, and (ii) the second registration between CBCT(t) and CBCT(0).

FIG. 20 illustrates image guided radiation treatment using x-ray source arrays according to a preferred embodiment. Any of the systems of FIGS. 13A-16 can be used in conjunction with the method of FIG. 20, provided there is at least one x-ray source array (XSA) included. Although not required for all cases, it is preferable that the x-ray source array XSA be dimensioned and configured within the imaging geometry of the treatment guidance imaging system such a tomosynthesis imaging arc of at least about 6 degrees can be provided by virtue of the spatial distribution of the x-ray point sources thereon, without requiring any rotation of the rotatable gantry structure. At step 2002, a pre-acquired image data set is received. At step 2004, during a patient setup interval, the patient is positioned into an initial treatment position relative to the IGRT system. At step 2006, at a first gantry angle, the x-ray source array XSA is operated to acquire a population of x-ray cone beam projection images of the body part. At step 2008, the first population of x-ray cone beam projection images is processed to compute a tomosynthesis reconstructed image volume. At step 2010, treatment radiation is delivered to the body part based at least in part on a comparison between the tomosynthesis reconstructed image volume and the pre-acquired image data set. Advantageously, meaningful 3D-based image guidance can be provided even where the rotatable gantry structure is stationary. This may be particularly useful in scenarios in which the treatment guidance system is attached to the same rotatable gantry structure as the radiation treatment head, and in which the radiation treatment plan requires the rotatable gantry structure to remain stationary for a period of time.

One or more aspects of the method of FIG. 20 can be carried out according to one or more of the methods described in the commonly assigned and concurrently filed U.S. Application No. 61/371,733, supra. For one preferred embodiment, comparing the intrafraction tomosynthesis reconstructed image, designated hereinbelow as tomo(t), with the pre-acquired image data set comprises computing a digitally reconstructed DRT image data set from the pre-acquired 3D image volume, processing the DRT image data set to compute a DRT image volume, and computing a registration between tomo(t) and the DRT image volume. Preferably, the DRT image data set is computed from the pre-acquired 3D image volume using virtual projections based on the same imaging geometry for which tomo(t) was acquired.

For one preferred embodiment in which the treatment guidance imaging system uses tomosynthesis imaging for both setup and in-treatment imaging, an initial tomosynthesis image volume tomo(0) is acquired, and a first registration between tomo(0) and a DRT image volume based on the pre-acquired image data set is carried out. The x-ray cone beam projection images from which tomo(0) is reconstructed are preferably acquired with the body part in an initial treatment position, or alternatively at some other starting point in time during setup, upon setup, or near a beginning of the treatment delivery, termed herein an initial time. Computation of the registration between tomo(t) and the DRT image volume is then based upon (i) the first registration between tomo(0) and the DRT image volume, and (ii) a second registration between tomo(t) and tomo(0).

For another preferred embodiment, comparison of tomo(t) to the pre-acquired image data set comprises a direct 3D-3D registration between tomo(t) and the pre-acquired image volume. For another preferred embodiment, the method of FIG. 18 can be used in conjunction with the method of FIG. 20, wherein an initial population of x-ray cone beam projection images is acquired at an initial time and used to construct an initial CBCT volume CBCT(0). A first registration is then performed between CBCT(0) and the pre-acquired image data set. During radiation delivery, for the most recent tomosynthesis volume tomo(t), there is identified a subset of the initial population of x-ray cone beam projection images that were used to construct CBCT(0) that correspond in tomosynthesis imaging arc to the tomosynthesis imaging arc for tomo(t), and an arc-matched tomosynthesis volume $tomo_{MATCHED(t)}(0)$ is computed therefrom. A second registration between tomo(t) and $tomo_{MATCHED(t)}(0)$ is computed, and then the desired registration between tomo(t) and the pre-acquired image volume is computed based on (i) the first registration between CBCT(0) and the pre-acquired image volume, (ii) the inherent registration between $tomo_{MATCHED(t)}(0)$ and CBCT(0), and (iii) the second registration between tomo(t) and $tomo_{MATCHED(t)}(0)$.

According to yet another preferred embodiment that can be used in conjunction with one or more of the above-described preferred embodiments, an IGRT system having dynamic switching capability between sliding-window tomosynthesis-based treatment guidance and sliding-window CBCT-based treatment guidance is provided. Subsequent to a patient setup interval, an x-ray cone beam imaging source and it associated detector are operated to acquire a population of x-ray cone beam projection images of the body part for a respective population of gantry angles and acquisition times. First information is received that is indicative of a selection between a tomosynthesis-based treatment guidance mode of operation and a CBCT-based treatment guidance mode. The first population of x-ray cone beam projection images is processed to compute therefrom a time sequence of sliding-window tomographic image volumes characterized in that each subsequent member of the time sequence is computed using at least one same x-ray cone beam projection image as used in computing at least one previous member of that time sequence, wherein the sliding-window tomographic image volume comprises one of (i) a tomosynthesis reconstructed image volume if the first information indicates the tomosynthesis-based treatment guidance mode, and (ii) a CBCT image volume if the first information indicates the CBCT-based treatment guidance mode. The radiation treatment head is operated to deliver treatment radiation to the body part based at least in part on a comparison between each of the time sequence of sliding-window tomographic image volumes and the pre-acquired image data set.

Optionally, the selection between tomosynthesis-based mode and CBCT-based mode is automatically and dynamically determined during radiation treatment delivery. A selection algorithm can be provided that makes the selection based upon one or more of: a data aging threshold; an acquisition rate of the x-ray cone beam projection images; a time separation between adjacent members of the time sequence; a rotational movement pattern of the rotatable gantry structure; an available number of x-ray cone beam projection images acquired within the data aging threshold of a most recent x-ray cone beam projection image acquisition; and a gantry angle distribution associated with the available number of x-ray cone beam projection images acquired within the data aging threshold of the most recent x-ray cone beam projection image acquisition. User inputs indicative of certain thresholds to be used in the decision process and/or operator overrides can optionally be provided.

Whereas many alterations and modifications of the present invention will no doubt become apparent to a person of ordinary skill in the art after having read the foregoing description, it is to be understood that the particular embodiments shown and described by way of illustration are in no way intended to be considered limiting. By way of example, although one or more preferred embodiments are described above in which the in-therapy imaging sources are distinct from the therapeutic radiation source, in other preferred embodiments the imaging system can be provided as a portal imaging system, in which an imaging detector is provided opposite the therapeutic radiation source relative to the isocenter.

By way of further example, with nonlimiting exemplary reference to FIG. 3B, supra, while the beam members 306 of the rotatable gantry structure 304 are described as extending between ring members 308 and 309 that are on opposite sides of the isocentric transverse plane 217, it is not outside the scope of the present teachings to provide a system in which the opposing ring members are on the same side of the isocentric transverse plane. In such cases, the opposing ring members would be separated by an amount sufficient to ensure mechanical stability (for example, 1 m-2 m depending on the choice of materials or other design criteria), while the isocenter could be positioned slightly outside the end of the central bore, which could potentially be useful for some therapy scenarios now known or hereinafter developed.

By way of still further example, the above-described teaching in which two kV imaging systems are mounted perpendicular to each other and acquire all of the X-ray images required for CBCT image reconstruction with only a 90 degree rotation, rather than a 180 degree rotation, of a rotatable structure on which they are mounted can be used on systems with a variety of different overall mechanical architectures, and therefore is within the scope of the present teachings as applied to a variety of different suitable overall architectures other than the particularly suitable mechanical architectures described hereinabove. By way of even further example, the teachings above relating to sliding CBCT reconstruction can be used on systems with a variety of different overall suitable mechanical architectures, and therefore is within the scope of the present teachings as applied to a variety of different overall suitable architectures other than the particularly suitable mechanical architectures described hereinabove. Therefore, reference to the details of the embodiments are not intended to limit their scope, which is limited only by the scope of the claims set forth below.

What is claimed is:

1. A radiation treatment apparatus, comprising:
   a gantry structure; and
   a radiation treatment head movably mounted to the gantry structure to allow gimballing of the radiation treatment head relative to the gantry structure, the gimballing comprising pivotable movement in at least one independent pivot direction defined with respect to the gantry structure, wherein the radiation treatment head has pivotable movement in a maximum angle range of +/−30 degrees to +/−45 degrees; and
   a patient couch operatively coupled with the radiation treatment head to provide movement of the patient couch relative to the radiation treatment head.

2. The radiation treatment apparatus of claim 1, wherein the patient couch and the radiation treatment head are movable to provide non-coplanar radiation treatment of a tissue volume.

3. The radiation treatment apparatus of claim 2, further comprising a controller operatively coupled with the patient couch and the radiation treatment head, where to provide non-coplanar radiation treatment of a tissue volume the controller configured to control movement of the patient couch and gimbaling of the radiation treatment head to position a radiation beam generated by the radiation treatment head at the tissue volume.

4. The radiation treatment apparatus of claim 1, wherein the patient couch is configured to manipulate the patient couch with three or more degrees of freedom.

5. The radiation treatment apparatus of claim 4, where the three or more degrees of freedom comprise three orthogonal translations and one rotation.

6. The radiation treatment apparatus of claim 1, where a transverse isocentric plane being defined that passes through the isocenter in a direction orthogonal to the rotation axis, wherein the pivotable movement is in at least two independent pivot directions including a first pivot direction around a first pivot axis generally parallel to the transverse isomeric plane and a second pivot direction around a second pivot axis nonparallel to the first pivot axis.

7. The radiation treatment apparatus of claim 1, wherein the gantry structure is a rotatable gantry structure.

8. The radiation treatment apparatus of claim 1, wherein the gimballing comprises pivotable movement in at least two independent pivot directions defined with respect to a beam member.

9. A method of operating a radiation treatment apparatus, comprising:
translating a radiation treatment head movably mounted to a gantry structure;
gimballing, by a processing unit, the radiation treatment head relative to the gantry structure, the gimballing comprising pivotably moving the radiation treatment head in at least one independent pivot direction defined with respect to the gantry structure, where gimballing comprises pivotably moving the radiation treatment head with a maximum angle of approximately +/−30 degrees; and
moving, by the processing unit, a patient couch relative to the radiation treatment head.

10. The method of claim 9, wherein moving the patient couch and gimballing the radiation treatment head enable non-coplanar radiation treatment of a tissue volume positioned near or around an isocenter of the radiation treatment apparatus.

11. The method of claim 9, wherein moving the patient couch comprises manipulating the patient couch with three or more degrees of freedom.

12. The method of claim 11, where the three or more degrees of freedom comprise three orthogonal translations and one rotation.

13. The method of claim 9, further comprising rotating the radiation treatment head relative to the gantry structure.

14. The method of claim 9, wherein gimballing comprises pivotably moving the radiation treatment head in at least two independent pivot directions defined with respect to the gantry structure.

15. A non-transitory machine readable medium that, when executed by a processing unit, cause the processing unit to:
translate a radiation treatment head movably mounted to a beam member of a gantry structure;
gimbal, by the processing unit, the radiation treatment head relative to the gantry structure, the gimballing comprising pivotally moving the radiation treatment head in at least one independent pivot direction defined with respect to the gantry structure, wherein the processing unit further to gimbal the radiation treatment head with a maximum angle of approximately +/−30 degrees; and
move a patient couch relative to the radiation treatment head.

16. The non-transitory machine readable medium of claim 15, wherein the processing unit to manipulate the patient couch with three or more degrees of freedom.

17. The non-transitory machine readable medium of claim 15, wherein the processing unit further to rotate the radiation treatment head relative to the beam member.

* * * * *